US006653346B1

(12) United States Patent
Wang et al.

(10) Patent No.: US 6,653,346 B1
(45) Date of Patent: Nov. 25, 2003

(54) CYTOPROTECTIVE BENZOFURAN DERIVATIVES

(75) Inventors: Bing Wang, Cupertino, CA (US); Jian Chen, Sunnyvale, CA (US)

(73) Assignee: Galileo Pharmaceuticals, Inc., Santa Clara, CA (US)

( * ) Notice: Subject to any disclaimer, the term of this patent is extended or adjusted under 35 U.S.C. 154(b) by 0 days.

(21) Appl. No.: 10/361,141

(22) Filed: Feb. 6, 2003

Related U.S. Application Data

(60) Provisional application No. 60/355,331, filed on Feb. 7, 2002, and provisional application No. 60/429,584, filed on Nov. 27, 2002.

(51) Int. Cl.[7] .................. A61K 31/34; C07D 307/91; C07D 307/78
(52) U.S. Cl. .................. 514/469; 514/468; 549/469; 549/468; 549/460
(58) Field of Search .................. 514/469, 468; 549/460, 468, 469

(56) References Cited

U.S. PATENT DOCUMENTS

| 4,714,711 A | 12/1987 | Miller et al. | |
|---|---|---|---|
| 4,800,228 A | 1/1989 | Adams et al. | |
| 4,863,958 A | 9/1989 | Belanger et al. | |
| 5,114,966 A | 5/1992 | Scuri et al. | |
| 5,480,645 A | 1/1996 | Della Valle et al. | |
| 5,674,876 A | 10/1997 | Gilbert et al. | |
| 5,719,167 A | 2/1998 | Doshi et al. | |
| 5,798,356 A | 8/1998 | Doshi | |
| 6,319,930 B1 * | 11/2001 | Lesieur et al. | 514/300 |
| 6,329,421 B1 * | 12/2001 | Prasit et al. | 514/443 |
| 6,355,669 B1 * | 3/2002 | Yamauchi et al. | 514/427 |
| 6,376,491 B1 * | 4/2002 | Aoki et al. | 514/235.5 |
| 6,391,897 B2 * | 5/2002 | Malamas et al. | 514/340 |
| 6,395,738 B1 * | 5/2002 | Ohshima et al. | 514/252.13 |
| 6,458,801 B1 * | 10/2002 | Carniato et al. | 514/275 |
| 6,479,536 B1 * | 11/2002 | Ohkawa et al. | 514/416 |
| 6,492,374 B2 * | 12/2002 | Andersen et al. | 514/254.09 |
| 6,515,015 B1 * | 2/2003 | Adams et al. | 514/443 |
| 6,552,071 B2 * | 4/2003 | Yuan et al. | 514/453 |
| 6,569,894 B1 * | 5/2003 | Takaki et al. | 514/469 |

FOREIGN PATENT DOCUMENTS

DE     2419729      11/1975

* cited by examiner

*Primary Examiner*—Deborah C. Lambkin
(74) *Attorney, Agent, or Firm*—Gloria Pfister

(57) ABSTRACT

Cytoprotective compounds, many of which are benzofuran derivatives are useful in the treatment of certain ischemic or inflammatory conditions, including but not limited to stroke, myocardial infarction, congestive heart failure, and skin disorders characterized by inflammation or oxidative damage. They are also useful in the manufacture of pharmaceutical and cosmetic formulations for the treatment of such conditions.

28 Claims, No Drawings

CYTOPROTECTIVE BENZOFURAN DERIVATIVES

CROSS-REFERENCES TO RELATED APPLICATIONS

This application claims priority to co-pending provisional applications U.S. Ser. No. 60/355,331 filed on Feb. 7, 2002, and U.S. Ser. No. 60/429,584 filed on Nov. 27, 2002, incorporated herein by reference.

FIELD OF THE INVENTION

The present invention relates to certain compounds having cytoprotective activity, and particularly to a series of benzofuran derivatives. The invention is also directed to formulations and methods for treating stroke, myocardial infarction and chronic heart failure, as well as other oxidative stress-related conditions that are typically responsive to cellular enzyme modulation. The invention is also directed to a method of treating inflammation by reducing C-reactive protein (CRP). The invention is also directed to cosmetic formulations for the treatment of skin inflammation and other skin disorders.

BACKGROUND INFORMATION

The present invention is concerned with cytoprotective compounds, which are benzofuran derivatives, said derivatives including steroisomers, mixtures of stereoisomers and therapeutically acceptable salts therof.

Compositions of the invention are active in certain experimental models that predict efficacy in, for example, certain ischemic or inflammatory conditions, including but not limited to stroke, myocardial infarction, congestive heart failure, and skin disorders characterized by inflammation or oxidative damage. The invention is therefore related to the use of the cytoprotective derivatives in such conditions.

2,3-Dihydro-5-oxy-4,6,7-trimethyl-2-optionally substituted alkyl benzofurans have been disclosed as antioxidizing pharmaceutical products having anti-ischemic properties in U.S. Pat. No. 5,114,966. Hydroxamines derivatives of 2,3-dihydrobenzofuran carboxy acids have been disclosed in U.S. Pat. No. 5,480,645. 2,3-Dihydrofuran derivatives useful in preventing and treating neovascularization have been disclosed in U.S. Pat. No. 5,719,167 and U.S. Pat. No. 5,798,356. 5-Hydroxybenzofurans have been disclosed for the treatment of a pathological cell proliferative disease in U.S. Pat. No. 5,674,876. A method of inhibiting mammalian leukotriene biosynthesis with 6-hydroxybenzofurans has been disclosed in U.S. Pat. No. 4,714,711.

While various agents have heretofore been provided for such conditions, it has, however, remained desired to provide new therapies for conditions characterized by oxidative stress, and particularly, for providing protection in the event of cerebral ischemia, ultraviolet exposure or inflammation; especially desired are agents that are effective even if first administered after a significant period of time (e.g., about 5 or more hours) following an ischemic or oxidative insult.

SUMMARY OF THE INVENTION

The present invention is concerned with certain novel and related cytoprotective compounds that are particularly active in restoring or preserving metabolic integrity in oxidatively competent cells that have been subjected to oxygen deprivation. Such compounds, predominantly benzofuran derivatives are useful in the manufacture of pharmaceutical compositions for treating a number of conditions characterized by oxidative stress, and particularly, in providing protection in the event of cerebral ischemia, ultraviolet exposure, or inflammation, even when administered a significant time interval after an ischemic or oxidative insult. In particular, the compositions of the present invention are useful in the treatment of stroke, as demonstrated by providing neuroprotection in a standard experimental model of focal cerebral ischemia. They are also useful in the treatment of myocardial ischemia (myocardial infarction), as well as other indications characterized by oxidative stress and/or inflammation, including, but not limited to, diabetes, renal disease, pre-menstrual syndrome, asthma, cardiopulmonary inflammatory disorders, chronic heart failure, rheumatoid arthritis, muscle fatigue, intermittent claudication, and for the preservation of allograft tissue for transplantation. Particularly with regard to dermatological conditions, the compounds, formulations and methods of the present invention are useful in regulating skin condition, regulating the signs of skin aging, and in treating a number of conditions, including, but not limited to preventing and protecting skin tissue against age-related damage or damage resulting from insults such as harmful (UV) radiation, stress and fatigue. These compounds, formulations and methods of the present invention are also useful in the treatment for example of contact dermatitis, acne, irritation including retinoid induced irritation, hirsutism, modulation of hair growth, disorders in pigmentation, or psoriasis, and can be used as bactericides, antifungal and antimicrobial agents. The compounds of the present invention also show activity for reducing elevated CRP levels associated with a number of diseases and disorders, including but not limited to, cardiovascular disease, diabetes and infectious diseases.

The present invention concerns the compounds represented by the Formula I:

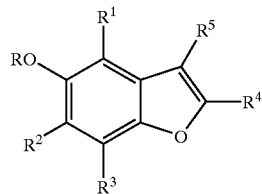

Formula I wherein:

$R^1$ is: hydrogen, optionally substituted alkyl, optionally substituted alkenyl, optionally substituted aryl, (optionally substituted alkoxy)carbonyl, or halogen;

$R^2$ and $R^3$ are independently selected from optionally substituted alkyl, optionally substituted alkenyl, or optionally substituted cycloalkyl;

$R^4$ is: hydrogen, optionally substituted aryl, (optionally substituted alkyl)carbonyl, (optionally substituted aryl) carbonyl, (optionally substituted heterocyclyl) carbonyl, (optionally substituted heterocyclylalkyl) carbonyl, (optionally substituted alkoxy)carbonyl, (optionally substituted alkenyloxy)carbonyl, (optionally substituted amino)carbonyo, carboxy, formyl, or hydroxy(optionally substituted)alkyl;

$R^5$ is: hydrogen, alkyl, alkenyl, (optionally substituted alkoxy)carbonyl, carboxy, (optionally substituted amino)carbonyl, or optionally substituted aryl;

provided that one of $R^4$ or $R^5$ is hydrogen, and that when $R^4$ is hydrogen $R^5$ is not hydrogen, and when $R^5$ is hydrogen $R^4$ is not hydrogen;

R is hydrogen, alkyl, acyl, phosphoryl, or polyalkoxy; or

R and $R^1$ with the atoms to which they are attached form an optionally substituted ring;
including single stereoisomers, mixtures of stereoisomers, and the pharmaceutically acceptable salts thereof.

A preferred embodiment of this invention concerns the compounds of Formula I where $R^2$ and $R^3$ are $(C_1-C_6)$-alkyl, preferably methyl, and within that subset those compounds of Formula I wherein R is hydrogen.

In another embodiment, the invention concerns the compounds of Formula I wherein $R^2$ and $R^3$ are $(C_1-C_6)$-alkyl, preferably methyl, R is hydrogen, $R^5$ is hydrogen, and $R^4$ is optionally substituted aryl, (optionally substituted alkyl)carbonyl, (optionally substituted aryl)carbonyl, (optionally substituted heterocyclyl)carbonyl, (optionally substituted heterocyclylalkyl)carbonyl, (optionally substituted alkoxy)carbonyl, (optionally substituted alkenyloxy)carbonyl, (optionally substituted amino)carbony), carboxy, formyl, or hydroxy(optionally substituted)alkyl, especially wherein said aryl is unsubstituted phenyl or substituted phenyl with one or more substitutents selected from alkyl, alkoxy, hydroxy, (optionally substituted alkoxy)carbonyl, nitro, halo, and cyano.

In another embodiment, the invention concerns the compounds of Formula I wherein $R^2$ and $R^3$ are $(C_1-C_6)$-alkyl, preferably methyl, R is hydrogen, $R^4$ is hydrogen, and $R^5$ is optionally substituted aryl, preferably unsubstituted phenyl or phenyl substituted with one or more substitutents selected from alkyl, alkoxy, hydroxy, (optionally substituted alkoxy)carbonyl, nitro, halo, and cyano.

In another embodiment, the invention concerns the compounds of Formula I wherein $R^2$ and $R^3$ form a ring, preferably R and $R^1$ form a furan ring substituted with an unsubstituted phenyl or with a phenyl substituted with one or more substitutents selected from alkyl, alkenyl, hydroxy, alkoxy, nitro, cyano, carboxy, carboxyester, haloalkyl, and halo.

Certain embodiments of the invention provide novel and preferred combinations of the substituents groups pendant from the formulae of the different inventions.

In another aspect, the invention relates to pharmaceutical and/or cosmetic compositions containing a therapeutically effective amount of a compound of any of Formula I, or a pharmaceutically acceptable salt thereof, admixed with at least one pharmaceutically acceptable excipient. Particularly preferred are those pharmaceutical or cosmetic compositions wherein a compound of Formula I is selected from the Preferred Compounds.

Another aspect of the present invention concerns methods of treatment for a mammal suffering from a condition characterized by oxidative stress by administering a therapeutically effective amount of a compound represented by the Formula I including single stereoisomers, mixtures of stereoisomers, and the pharmaceutically acceptable salts thereof.

In one embodiment, the invention relates to a method of treatment of a cardiovascular, cerebrovascular, neurologic, inflammatory, autoimmune, and/or dermatologic condition. In another embodiment the invention relates to a condition selected from stroke, cerebral ischemia, myocardial infarction, chronic heart failure, retinal ischemia, post-surgical cognitive diysfunctions, peripheral neuropathy, spinal cord injury, head injury and surgical trauma. In another embodiment the condition involves inflammatory or auto-mimmune components.

In another embodiment, the invention relates to a method for treating dermatologic conditions characterized by oxidative stress including but not limited to regulating skin condition, regulating the signs of skin aging, contact dermatitis, acne, skin pigmentation, hair growth modulation, irritation including retinoid induced irritation, psoriasis, age-related damage and damage resulting from harmful (UV) radiation, stress, or fatigue. In another embodiment the compound of Formula I or composition thereof, is administered topically. In another embodiment the condition is dermatologic, further comprising a method of promoting a product by directing a user to apply to the skin a pharmaceutical or cosmetic composition incorporating said compound of Formula I.

In still another embodiment, the invention relates to a method of treating stroke and other oxidative stress-related conditions that are responsive to cellular enzyme modulation such as cerebral ischemia, myocardial infarction, chronic heart failure, and exposure to UV radiation in a mammal, by administering to a mammal in need of such treatment a therapeutically effective amount of a compound of any of Formula I, or a pharmaceutically acceptable salt thereof.

In still another aspect, the invention relates to a method of reducing levels of C-reactive protein (CRP) associated with inflammation, including but not limited to cardiovascular inflammatory condition, respiratory inflammatory condition, sepsis, diabetes, muscle fatigue, systemic lupus erythematosis (SLE), end stage renal disease (ERSD), periodontal disease, and inflammatory skin conditions.

Particularly preferred are those methods of treatment and uses in the manufacture of pharmaceutical and/or cosmetic compositions therefor, wherein a compound of Formula I is selected from the Preferred Compounds.

DETAILED DESCRIPTION OF THE INVENTION

Definitions

As used in the present specification, the following words and phrases are generally intended to have the meanings as set forth below, except to the extent that the context in which they are used indicates otherwise.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns that are sterically impractical and/or synthetically non-feasible.

Certain compound, reactant, or reaction parameter abbreviations are defined as follows:

"DCM" refers to dichloromethane or methylene chloride

"t-Bu" refers to t-butyl

"DCC" refers to 1,3-dicyclohexylcarbodiimide

"DIC" refers to N,N-diisopropylcarbodiimide

"DIPEA" refers to diisopropyl ethylamine

"DMAP" refers to 4-N,N-dimethylamino pyridine

"DMF" refers to N,N-dimethyl formamide

"Eq." refers to equivalent

"EDCI" refers to 1-(3-dimethylaminopropyl)-3-ethylcarbodiimide hydrochloride

"MeOH" refers to methanol

"THF" refers to tetrahydrofuran

"EtOAc" refers to ethyl acetate.

The term "acyl" refers to the groups —C(O)—H, —C(O)-(optionally substituted alkyl), —C(O)-(optionally substituted cycloalkyl), —C(O)-(optionally substituted alkenyl), —C(O)-(optionally substituted cycloalkenyl), —C(O)-(optionally substituted aryl), —C(O)-(optionally substituted heteroaryl) and —C(O)-(optionally substituted heterocyclyl).

The term "alkenyl" refers to a monoradical branched or unbranched, unsaturated or polyunsaturated hydrocarbon chain, having from about 2 to 20 carbon atoms, more preferably about 2 to 10 carbon atoms. This term is exemplified by groups such as ethenyl, but-2-enyl, 3-methyl-but-2-enyl (also referred to as "prenyl"), octa-2,6-dienyl, 3,7-dimethyl-octa-2,6-dienyl (also referred to as "geranyl"), and the like.

The term "substituted alkenyl" refers to an alkenyl group in which 1 or more (up to about 5, preferably up to about 3) hydrogen atoms is replaced by a substituent for example: hydroxy, alkoxy, carboxy, cyano, halogen or nitro.

The term "alkoxy" refers to the groups —O-alkyl, —O-alkenyl, —O-cycloalkyl, —O-cycloalkenyl, and —O-alkynyl. Preferred alkoxy groups are —O-alkyl and —O-alkenyl and include, by way of example, methoxy, ethoxy, n-propoxy, iso-propoxy, n-butoxy, tert-butoxy, sec-butoxy, n-pentoxy, n-hexoxy, 1,2-dimethylbutoxy, 3,7-dimethyl-octa-2,6-dienyloxy and the like.

The term "substituted alkoxy" refers to the groups —O-(substituted alkyl), —O-(substituted alkenyl), —O-(substituted cycloalkyl), —O-(substituted cycloalkenyl), —O-(substituted alkynyl) and —O-(optionally substituted alkylene)-alkoxy. One preferred substituted alkoxy group is "polyalkoxy" or —O-(substituted alkylene)-alkoxy, and includes groups such as —OCH$_2$OCH$_3$, —OCH$_2$CH$_2$OCH$_3$, and (or PEG) groups such as —O(CH$_2$CH$_2$O)$_x$CH$_3$ and —O(CH$_2$CH$_2$O)$_x$H where x is an integer of about 2–20, preferably about 2–10, and more preferably about 2–5.

The term "alkyl" refers to a monoradical branched or unbranched saturated hydrocarbon chain preferably having from about 1 to 20 carbon atoms, more preferably about 1 to 10 carbon atoms, and even more preferably about 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group in which 1 or more (up to about 5, preferably up to about 3) hydrogen atoms is replaced by a substituent independently selected from the group: =O, =S, acyl, acyloxy, optionally substituted alkoxy, optionally substituted amino, azido, carboxyl, (optionally substituted alkoxy)carbonyl, (optionally substituted amino)carbonyl, cyano, optionally substituted cycloalkyl, optionally substituted cycloalkenyl, heterocyclyl, carboxy, halogen, hydroxyl, nitro, cyano, sulfanyl, sulfinyl, and sulfony, or two substituents with the carbon to which they are attached may form a ring. One of the preferred optional substituents for alkyl is hydroxy, exemplified by hydroxyalkyl groups, such as 2-hydroxyethyl, 3-hydroxypropyl, 3-hydroxybutyl, 4-hydroxybutyl, and the like; dihydroxyalkyl groups (glycols), such as 2,3-dihydroxypropyl, 3,4-dihydroxybutyl, 2,4-dihydroxybutyl, and the like; and those compounds known as polyethylene glycols, polypropylene glycols and polybutylene glycols, and the like. A preferred "substituted alkyl" wherein the substitutents form a ring is 6-hydroxy-3-methyl-[1,3]oxazinan-6-yl.

The term "amino" refers to the group —NH$_2$.

The term "substituted amino" refers to the group —NHR or —NRR where each R is independently selected from the group: optionally substituted alkyl, optionally substituted cycloalkyl, optionally substituted alkenyl, optionally substituted cycloalkenyl, optionally substituted alkynyl, optionally substituted aryl, optionally substituted heteroaryl, optionally substituted heterocyclyl, acyl, optionally substituted alkoxy, carboxy and alkoxycarbonyl, and wherein RR form with the nitrogen to which they are attached a cyclic amine optionally incorporating one or more additional heteroatoms selected from O, N and S.

The term "aryl" refers to an aromatic cyclic hydrocarbon group of from 6 to 20 carbon atoms having a single ring (e.g., phenyl) or multiple condensed (fused) rings (e.g., naphthyl or anthryl). Preferred aryls include phenyl, naphthyl and the like.

The term "substituted aryl" refers to an aryl group as defined above, which unless otherwise constrained by the definition for the aryl substituent, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as trihalomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydroxyl, nitro, sulfanyl, sulfinyl, and sulfonyl. Preferred aryl substituents include optionally substituted alkenyl, alkyl, alkoxy, substituted amino, halo, hydroxy, alkoxycarbonyl, carboxy, cyano, nitro, phosphoryl.

The term "carbonyl" refers to the di-radical "—C(=O)—", which is also illustrated as "—C(O)—".

The term "(optionally substituted alkoxy)carbonyl" refers to the groups: —C(O)O-(optionally substituted alkyl), —C(O)O-(optionally substituted cycloalkyl), —C(O)O-(optionally substituted alkenyl), —C(O)O-(optionally substituted alkynyl), —C(O)O-(optionally substituted aryl), —C(O)O-(optionally substituted heteroaryl), and —C(O)O-(optionally substituted heterocyclyl). These moieties are also referred to as esters.

The term "(optionally substituted amino)carbonyl" refers to the group —C(O)-(optionally substituted amino). This moiety is also referred to as a primary, secondary or tertiary carboxamide, and the "substituted amino" can be a cyclic amine.

The term "carboxy" or "carboxyl" refers to the moiety "—C(O)OH", which is also illustrated as "—COOH".

The term "compound of Formula I" is intended to encompass the derivatives of the invention as disclosed, and/or the pharmaceutically acceptable salts of such compounds. In addition, the compounds employed in this invention include the individual stereochemical isomers (arising from the selection of substituent groups) and mixtures of isomers.

The term "cosmetics" includes make-up, foundation, and skin care products. The term "make-up" refers to products that leave color on the face, including foundations, blacks and browns, i.e., mascara, concealers, eye liners, brow colors, eye shadows, blushers, lip colors, and so forth. The term "foundation" refers to liquid, creme, mousse, pancake, compact, concealer or like products that even out the overall coloring of the skin. Foundation is typically manufactured to work better over moisturized and/or oiled skin. The term "skin care products" refers to products used to treat or otherwise care for, moisturize, improve, or clean the skin.

Products contemplated by the phrase "skin care products" include, but are not limited to, adhesives, bandages, toothpaste, anhydrous occlusive moisturizers, antiperspirants, deodorants, powder laundry detergent, fabric softener towels, occlusive drug delivery patches, nail polish, powders, tissues, wipes, solid emulsion compact, anhydrous hair conditioners medicated shampoos, scalp treatments and the like.

The term "CRP" or "C-reactive protein" refers to a biochemical marker of inflammation. The presence of elevatel levels of CRP has been shown to be associated with various inflammatory conditions such as for example, cardiovascular diseases or disorders, including atrial fibrillation, unstable angina, coronary artery disease, peripheral artery disease, cardiac allograft vasculopathy (CAVD); mastitis; preclampsia; inflammatory bowel conditions; stroke; tissue infarction; lumbosciatic; estrogen/progestin hormone replacement therapy (HRT); infection (bacterial, viral and protozoan); bacterial meningitis; trauma; surgery; biomaterial implants; smoking; obesity; neurodegenerative diseases such as, Alzheimers; infectious disease, such as, for example, myocarditis, cardiomyopathy, acute endocarditis, pericarditis; atherosclerosis; Systemic Inflammatory Response Syndrome (SIRS)/sepsis; adult respiratory distress syndrome (ARDS); asthma; rheumatoid arthritis, osteoarthritis, systemic lupus erythematosis; Airway hyper-responsiveness (AHR); bronchial hyper-reactivity; Chronic Obstructive Pulmonary disease (COPD); Congestive Heart Failure (CHF); inflammatory complications of diabetes mellitus type I and type II; metabolic syndrome; end stage renal disease (ESRD), pre-menstrual syndrome (PMS) or muscle fatigue or inflammation; multiple organ dysfunction syndrome (MODS); airway hyper-responsiveness (AHR); bronchial hyper-reactivity; aging; acute allergic reactions; gingivitis and dermal conditions. CRP has been reported as a marker for systemic inflammation Spanheimer (2001, *Postgrad. Med.* 109 (4) 26) and Ridkler et al (2000, *N.E.J.M.* 342 (12) 83643).

The term "cycloalkyl" refers to the monovalent saturated radical consisting of one or more rings, which can optionally be susbstituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino or sulfonyl, unless otherwise indicated. Examples of cycloalkyl radicals include but are not limited to, cyclopropyl, cyclopentyl, cyclohexyl, etc.

The term "dermatologically-acceptable," as used herein, means that the compositions or components thereof so-described are suitable for use in contact with human skin without undue toxicity, incompatibility, instability, allergic response, or the like.

The term "halo" or "halogen" refers to fluoro, chloro, bromo and iodo.

The term "heteroaryl" refers to an aromatic cyclic hydrocarbon group having about 1 to 40 (preferably from about 3 to 15) carbon atoms and about 1 to 10 hetero atoms (preferably about 1 to 4 heteroatoms, selected from nitrogen, sulfur, phosphorus, and/or oxygen) within at least one ring. Such heteroaryl groups can have a single ring (e.g., pyridyl or furyl) or multiple condensed rings (e.g., indolizinyl or benzothienyl). Preferred heteroaryls include pyridyl, [2,2'] bipyridinyl, pyrrolyl and furyl.

The terms "heterocycle", "heterocyclic" and "heterocyclyl" refer to a monoradical, saturated or unsaturated, non-aromatic cyclic hydrocarbon group having about 1 to 40 (preferably from about 3 to 15) carbon atoms and about 1 to 10 hetero atoms (preferably about 1 to 4 heteroatoms, selected from nitrogen, sulfur, phosphorus, and/or oxygen) within the ring. Such heterocyclic groups can have a single ring or multiple condensed rings. Preferred heterocyclics include morpholino, piperidinyl, 1,3-oxazinane,and the like.

The terms "substituted heterocycle", "substituted heterocyclic" and "substituted heterocyclyl" refer to a heterocyclyl group as defined above, which unless otherwise constrained by the definition for the heterocycle, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocloooxy, hydroxyl, nitro, sulfanyl, sulfinyl, and sulfonyl.

The term "heterocycloalkyl" refers to the moiety "-alkylene-heterocycle" each having the meaning as defined herein.

The term "substituted heterocycloalkyl" refers to the moiety "-(optionally substituted aklylene)-(optionally substituted heterocycle)", each having the meaning as defined herein.

The term "inflammation", "inflammatory conditions", or "inflammation conditions" includes but is not limited to muscle fatigue, osteoarthritis, rheumatoid arthritits, inflammatory bowel syndrome or disorder, skin inflammation, such as atopic dermatitis, contact dermatitis, allergic dermatitis, xerosis, eczema, rosacea, seborrhea, psoriasis, atherosclerosis, thermal and radiation burns, acne, oily skin, wrinkles, excessive cellulite, excessive pore size, intrinsic skin aging, photo aging, photo damage, harmful UV damage, keratinization abnormalities, irritation including retinoid induced irritation, hirsutism, alopecia, dyspigmentation, inflammation due to wounds, scarring or stretch marks, loss of elasticity, skin atrophy and gingivitis.

The term "ischemia" refers to deficiency of blood to an organ or tissue due to functional constriction or actual obstruction of a blood vessel. Cerebral ischemia, also known as stroke, usually results from the interruption or reduction of blood and oxygen to the blood vessels of the brain; more rarely this may be the result of an hemorrhage. Signs of stroke include paralysis, slurred speech, general confusion, impairment of gait, cortical sensory loss over toes, foot and leg, and urinary incontinence, to name just a few. Many types of heart disease including cardiac arrhythmias or diseases due to cardiac structural abnormalities may produce cerebral emboli. Atrial fibrillation from any cause, including rheumatic valvular disease, may result in emboli being produced which can migrate into the arteries of the brain. Emboli formation and migration can occur as a result of arteriosclerotic cardiovascular disease and myocardial infarction. Emboli formation is also a definite risk for intracardiac surgery and prosthetic valve replacement. Heart bypass surgery and angioplasty can result in the formation of microemboli which can migrate into the arteries of the brain and cause a series of occlusions in a number of arteries, resulting in mental impairment. Cerebral embolism is also the principal complication in the transplant of artificial hearts. Furthermore, the overall risk of stroke after any type of general surgery is 0.2 to 1 percent. The vegetations of acute and subacute bacterial endocarditis can give rise to emboli which can occlude a major intracranial artery. Populations at risk of ischemia include but are not limited to patients scheduled for coronary arterial bypass graft surgery (CABG), patients at risk for postoperative complications, patients with subarachnoid hemorrhage (SAH), patients with a first or second ischemic stroke, patients with acute ischemic stroke, patients undergoing cardiopulmonary resuscitation (CPR), patients with temporary lobectomy, patients with dominant hemisphere resection, patients receiving prophylactic brain radiation, patients with closed head trauma with neurological loss, patients with microvascular multi-infarct dementia, patients with homozygous and heterozygous MELAS (Mitochondrial myopathy, encephalopathy, lactacidosis, stroke); patients with atherosclerotic or progressive supranuclear palsy disease, patients with symptomatic and asymptomatic Huntington's disease, patients with neonatal asphyxia, patients with meningitis or encephalitis, patients with post herpetic neuropathy, patients with intermittent claudication, patients with spinal cord injury, patients with Huntington's disease, Amyotrophic Lateral Sclerosis (ALS) or Friedreich's ataxia, patients with diabetic neuropathy or patients with a disease associated with a hypercoagulable state secondary to systemic disease, carcinoma, vasoconstriction (including reversible cerebral vasoconstriction, e.g. migraine, trauma, idiopathy), or venous conditions (including dehydration, pulmonary embolism, pericranial infection, postpartum and postoperative states and system cancer).

The term "personal care products" refer to health and cosmetic beauty aid products generally recognized as being formulated for beautifying and grooming the skin and hair. For example, personal care products include sunscreen products (e.g., lotions, skin creams, etc.), cosmetics, toiletries, and over-the-counter pharmaceutical products intended for topical usage.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts which retain the biological effectiveness and properties of the compounds of this invention and which are not biologically or otherwise undesirable. In many cases, the compounds of this invention are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "phosphoryl" refers to the group —P(O)(OR")$_2$, where R" is independently selected from hydrogen or alkyl and aryl, which group is sometimes also referred to as "phosphono" or as a "phosphate" or "phosphonic acid."

"Regulating skin condition" includes prophylactically regulating and/or therapeutically regulating skin condition, including visible and/or tactile discontinuities in skin such as, but not limited to, regulating visible and/or tactile discontinuities in the texture of skin, reducing post-inflammatory hyperpigmentation, regulating non-melanin discoloration of skin, regulating moisturization and barrier properties of skin, regulating epidermal differentiation of skin, regulating exfoliation of skin, thickening of skin to reduce skin atrophy, regulating the elasticity of skin, reducing oily skin, regulating cellulite in skin, regulating pruritus in skin, and promoting wound healing in skin. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, discontinuities in skin. Regulating skin condition involves improving skin appearance and/or feel. Regulating skin condition includes modulation body/cranial hair growth, including retarding and/or preventing the growth of body and/or head hair. Regulating skin condition includes regulating irritation including retinoid induced irritation. As used herein regulating the skin includes the use of the compounds of the invention as bactericides, antifungal and antimicrobial agents.

"Regulating the signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign). As used herein, prophylactically regulating such signs includes delaying, minimizing and/or preventing signs of skin aging. As used herein, therapeutically regulating such signs includes ameliorating, e.g., diminishing, minimizing and/or effacing signs of skin aging.

"Signs of skin aging" include, but are not limited to, all outward visibly and tactilely perceptible manifestations as well as any other macro or micro effects due to skin aging.

Such signs may be induced or caused by intrinsic factors or extrinsic factors, e.g., chronological aging and/or environmental damage (e.g., sunlight, UV, smoke, ozone, pollutants, stress, etc.). These signs may result from processes which include, but are not limited to, the development of textural discontinuities such as wrinkles, including both fine superficial wrinkles and coarse deep wrinkles, skin lines, facial frown lines, expression lines, rhytides, dermatoheliosis, photodamage, premature skin aging, crevices, bumps, pits, large pores (e.g., associated with adnexal structures such as sweat gland ducts, sebaceous glands, or hair follicles), "orange-peel" skin appearance, dryness, scaliness, flakiness and/or other forms of skin unevenness or roughness; blemishes such as acne, pimples, breakouts; excess skin oil problems such as over production of sebum, oiliness, facial shine, foundation breakthrough; abnormal desquamation (or exfoliation) or abnormal epidermal differentiation (e.g., abnormal skin turnover) such as scaliness, flakiness, keratoses, hyperkeratinization; inadequate skin moisturization (or hydration) such as caused by skin barrier damage, environmental dryness; loss of skin elasticity (loss and/or inactivation of functional skin elastin) such as elastosis, sagging (including puffiness in the eye area and jowls), loss of skin firmness, loss of skin tightness, loss of skin recoil from deformation; non-melanin skin discoloration such as undereye circles, blotching (e.g., uneven red coloration due to, e.g., rosacea), sallowness (pale color), discoloration caused by telangiectasia or spider vessels; melanin-related hyperpigmented (or unevenly pigmented) skin regions such as age spots (liver spots, brown spots) and freckles; post-inflammatory hyperpigmentation such as that which occurs following an inflammatory event (e.g., as an acne lesion, in-grown hair, insect/spider bite or sting, scratch, cut, wound, abrasion, and the like); atrophy such as, but not limited to, that associated with aging or steroid use; other histological or microscopic alterations in skin components such as ground substance (e.g., hyaluronic acid, glycosaminoglycans, etc.), collagen breakdown and structural alterations or abnormalities (e.g., changes in the stratum corneum, dermis, epidermis, the skin vascular system such as telangiectasia or spider vessels); tissue responses to insult such as itch or pruritus; and alterations to underlying tissues (e.g., subcutaneous fat, cellulite, muscles, trabeculae, septae, and the like), especially those proximate to the skin.

The term "therapeutically effective amount" refers to that amount of a compound of any of Formula I that is sufficient to effect treatment, as defined below, when administered to a mammal in need of such treatment. The therapeutically effective amount will vary depending upon the subject and disease condition being treated, the weight and age of the subject, the severity of the disease condition, the particular compound chosen, the dosing regimen to be followed, timing of administration, the manner of administration and the like, all of which can readily be determined by one of ordinary skill in the art.

The term "treatment" or "treating" means any treatment of a disease or disorder in a mammal, including:

preventing or protecting against the disease or disorder, that is, causing the clinical symptoms not to develop;

inhibiting the disease or disorder, that is, arresting or suppressing the development of clinical symptoms; and/or relieving the disease or disorder that is causing the regression of clinical symptoms.

It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

The term "topical application", as used herein, means to apply or spread the compositions of the present invention onto the surface of the skin.

Nomenclature

In general the nomenclature used in this Application is based on Autonom™ v.2.1, a Beilstein Institute computerized system for the generation of IUPAC systematic nomenclature.

The compounds of the present invention are named and numbered as described below.

Formula Ia

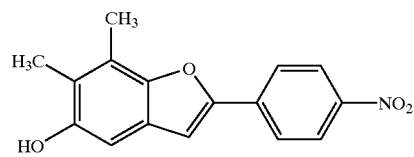

Formula Ia represents the compound according to formula I where R, $R^1$ and $R^5$ are hydrogen, $R^2$ and $R^3$ are methyl, and $R^4$ is p-nitro-phenyl, and can be named 6,7-dimethyl-2-(4-nitro-phenyl)-benzofuran-5-ol.

Formula Ib

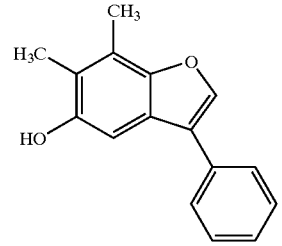

Formula Ib represents the compound according to formula I where R, $R^1$, and $R^4$ are hydrogen, $R^2$ and $R^3$ are methyl, and $R^5$ is phenyl, and can be named 6,7-dimethyl-3-phenyl-benzofuran-5-ol.

Synthesis of the Compounds of the Invention

Synthetic Reaction Parameters

The terms "solvent", "inert organic solvent" or "inert solvent" mean a solvent inert under the conditions of the reaction being described in conjunction therewith. Solvents employed in synthesis of the compounds of the invention include, for example, methanol, acetone, water, acetonitrile, 1,4-dioxane, dimethylformamide ("DMF"), benzene, toluene, xylene, tetrahydrofuran ("THF"), chloroform, methylene chloride (or dichloromethane, ("DCM")), diethyl ether, pyridine and the like, as well as mixtures thereof. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Unless specified to the contrary, the reactions described herein take place at atmospheric pressure within a temperature range from −10° C. to 110° C. (preferably from 0° C. to 40° C.; most preferably at "room" or "ambient" temperature, e.g., 20° C.). Further, unless otherwise specified, the reaction times and conditions are intended to be approximate, e.g., taking place at about atmospheric pressure within a temperature range of about −10° C. to about 110° C. (preferably from about 0° C. to about 40° C.;

most preferably at about "room" or "ambient" temperature, e.g., approximately 20° C.) over a period of about 1 to about 10 hours (preferably about 5 hours). Parameters given in the Examples are intended to be specific, not approximate.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Starting Materials

The starting compounds, e.g., 2,3-dimethylhydroquinone, are commercially available, e.g. from Aldrich Chemical Company, Milwaukee, Wis., or may be readily prepared by those skilled in the art using commonly employed methodology.

substituted ethanone in the presence of a base, followed by cyclization in the presence of an acid, can give a compound of Formula 105.

Reaction Scheme 2

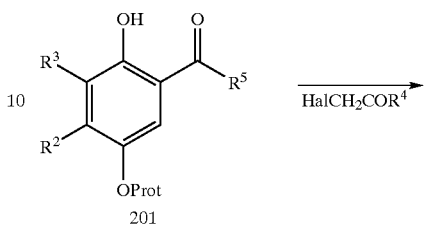

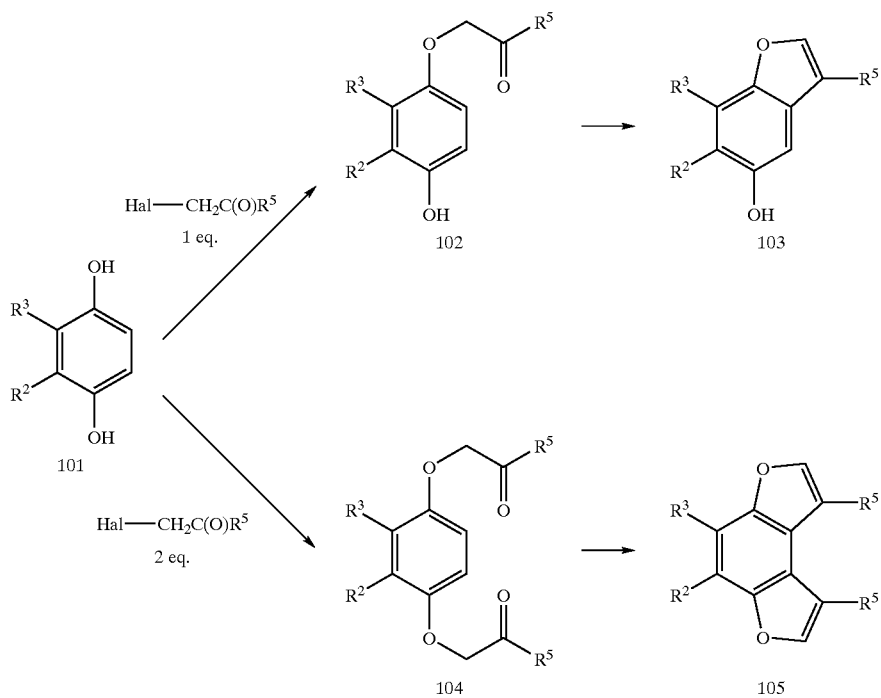

Reaction Scheme 1

Referring to Reaction Scheme 1, a 2,3-substituted hydroquinone of Formula 101 is treated with one equivalent of a 2-halo-1-substituted-ethanone, preferably 2-bromo-1-substituted-ethanone, most preferably 2-bromo-1-substituted phenyl ethanone, in the presence of a base such as sodium carbonate, potassium carbonate or cesium carbonate in a solvent such as acetone, THF, or DMF, to give 2-(4-hydroxy-2,3-substituted-phenoxy)-1-substituted-ethanone of Formula 102. Compound of Formula 102 can subsequently be treated with an acid such as polyphosphoric acid, hydrochloric acid, or sulfuric acid in an inert solvent such as toluene or xylene, to cyclise into a benzofuran compound of Formula 103.

Similarly treating a 2,3-substituted hydroquinone of Formula 102 with 2 or more equivalents of a 2-halo-1-

-continued

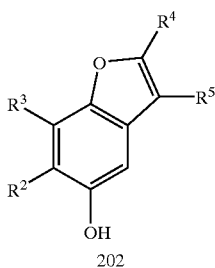

Referring to Scheme 2, a compound of Formula 201 wherein "Prot" is a hydroxy protecting group, preferably a tetrahydropyranyl group, when reacted with a 2-halo-1-substituted ethanone, preferably a 2-bromo-1-substituted ethanone in the presence of a base such as sodium carbonate, potassium carbonate, or cesium carbonate in a solvent such as acetone, THF, or DMF, followed by cyclization in the presence of an acid as described in reaction scheme 1, can give a compound of Formula 202.

Preferred Compounds

The following combinations and permutations of substituent groups (sub-grouped, respectively, in increasing order of preference) define compounds that are preferred as compositions of matter and compounds for use in the methods and pharmaceutical and cosmetic compositions according to the invention.

The compounds of any of Formula I where $R^2$ and $R^3$ are optionally substituted alkyl, particularly those wherein $R^2$ and $R^3$ are methyl.

Preferably those where $R^1$ is hydrogen or halogen

Especially those where R is hydrogen.

The compounds of any of Formula I where $R^1$ is hydrogen or halo

Preferably those where RX is hydrogen

The compounds of any of Formula I where R is hydrogen, alkyl, acyl, phosphoryl or polyalkoxy, preferably hydrogen, and $R^1$ is hydrogen 1. Particularly those wherein $R^2$ and $R^3$ are methyl Especially those of Formula I where $R^5$ is optionally substituted aryl, wherein the substitutents are chosen from alkyl, alkoxy, hydroxy, (optionally substituted alkoxy) carbonyl, nitro, halo, and cyano Particularly those where $R^5$ is optionally substituted phenyl.

Particularly those where $R^5$ is optionally substituted phenyl and $R^4$ is hydrogen.

Especially those of Formula I where $R^4$ is optionally substituted aryl

Particularly those where $R^4$ is optionally substituted phenyl

Preferably those where $R^4$ is para-substituted phenyl, wherein the substitutents are chosen from alkyl, alkoxy, hydroxy, (optionally substituted alkoxy)carbonyl, nitro, halo, and cyano Preferably those where $R^4$ is 4-nitrophenyl, 4-cyanophenyl and $R^5$ is hydrogen.

Especially those of Formula I where $R^4$ is formyl, (optionally substituted alkyl)carbonyl, (optionally substituted aryl)carbonyl, (optionally substituted heterocyclyl) carbonyl, (optionally substituted heterocyclylalkyl)carbonyl Particularly those where $R^4$ is (optionally substituted aryl)carbonyl Particularlyl those where $R^4$ is (optionally substituted alkyl)carbonyl Particularly those where $R^4$ is alkylcarbonyl optionally substituted with halogen, hydroxy or heterocyclyl, especially substituted with morpholin-1-yl Particularly those where $R^4$ is formyl Preferably those where $R^4$ is selected from formyl, phenylcarbonyl, bromoacetyl, morpholin-1-yl-acetyl, and acetyl; and $R^5$ is hydrogen Especially those wherein $R^4$ is (optionally substituted alkoxy)carbonyl, (optionally substituted alkenyloxy) carbonyl, (optionally substituted amino)carbonyl, carboxy, or hydroxy(optionally substituted)alkyl;

Particularly those where $R^4$ is (optionally substituted alkoxy)carbonyl, preferably those where the alkoxy is polyalkoxy, or (optionally substituted alkenyloxy) carbonyl, preferably those where the alkenyloxy is geranyloxy.

Particularly those where $R^4$ is (optionally substituted amino)carbonyl, preferably those wherein the amino is substituted with optionally substituted alkyl, especially hydroxyalkyl, or wherein the amino is a cyclic amine.

Preferably those where $R^4$is morpholin-1-yl-carbonyl; bis-(2-hydroxy-ethyl)-amide, 2-hydroxy-ethylamide, carboxylic acid; carboxylic acid methyl ester; carboxylic acid 3,7-dimethyl-octa-2,6-dienyl ester; [2-(2-methoxy-ethoxy)-ethoxy]ethyl ester; and $R^5$ is hydrogen.

Especially those where $R^4$ are hydroxy (optionally substituted) alkyl

Particularly where $R^4$ is hydroxymethyl, 1-hydroxy-2-morpholiny4-yl ethyl or 6-hydroxy-3-methyl-[1,3] oxazinan-6-yl.

The compounds of any of Formula I wherein R and $R^1$ with the atoms to which they are attached form an optionally substituted ring Especially those wherein R and $R^1$ with the atoms to which they are attached form a furan ring substituted with an unsubstituted phenyl ring or with a substituted phenyl ring, wherein one or more substituents are independently selected from alkyl, alkenyl, halo alkyl, hydroxy, alkoxy, carboxy, ester, haloalkyl, and halo.

The compounds preferred for use in the invention include the following, as well as their stereoisomers, salts, and mixtures thereof (as appropriate):

(5-Hydroxy-3,6,7-trimethyl-benzofuran-2-yl)-phenylmethanone;

(5-Hydroxy-6,7-dimethyl-benzofuran-2-yl)-morpholin-4-yl-methanone;

1-(5-Hydroxy-6,7-dimethyl-benzofuran-2-yl)-ethanone;

Acetic acid 2-(2-bromo-acetyl)-6,7-dimethyl-benzofuran-5-yl ester;

2-(1-Hydroxy-2-morpholin4-yl-ethyl)-6,7-dimethyl-benzofuran-5-ol;

Acetic acid 6,7-dimethyl-2-(2-morpholiin-1-yl-acetyl)-benzofuran-5-yl ester;

Acetic acid 2-(6-hydroxy-3-methyl-[1,3]oxazinan-6-yl)-6,7-dimethyl-benzofuran-5-yl ester;

1-(5-Hydroxy-6,7-dimethyl-benzofuran-2-yl)-2-morpholin-4-yl-ethanone;

1-(4-Bromo-5-hydroxy-6,7-dimethyl-benzofuran-2-yl)-ethanone;

2-Hydroxymethyl-6,7-dimethyl-benzofuran-5-ol;

6,7-Dimethyl-3-phenyl-benzofuran-5-ol;

6,7-Dimethyl-2-(4-nitro-phenyl)-benzofuran-5-ol;

5-Hydroxy-6,7-dimethyl-benzofuran-2-carbaldehyde;

4-(5-Hydroxy-6,7-dimethyl-benzofuran-2-yl)-benzonitrile;

5-Hydroxy-6,7-dimethyl-benzofuran-2-carboxylic acid;

5-Hydroxy-6,7-dimethyl-benzofuran-2-carboxylic acid methyl ester;

5-Hydroxy-6,7-dimethyl-benzofuran-2-carboxylic acid 3,7-dimethyl-octa-2,6-dienyl ester;

5-Hydroxy-6,7-dimethyl-benzofuran-2-carboxylic acid bis-(2-hydroxy-ethyl)-amide;

5-Hydroxy-6,7-dimethyl-benzofuran-2-carboxylic acid 2-[2-(2-methoxy-ethoxy)-ethoxy]-ethyl ester;

5-Hydroxy-6,7-dimethyl-benzofuran-2-carboxylic acid (2-hydroxy-ethyl)-amide;

3-(4-Methoxy-phenyl)-6,7-dimethyl-benzofuran-5-ol;

3-(4-Chloro-phenyl)-6,7-dimethyl-benzofuran-5-ol;

3-(4-Fluoro-phenyl)-6,7-dimethyl-benzofuran-5-ol;
4,5-Dimethyl-1,8-diphenyl-benzo[1,2-b;4,3-b']difuran;
1,8-Bis-(4-fluoro-phenyl)-4,5-dimethyl-benzo[1,2-b;4,3-b']difuran; and
1,8-Bis-(4-methoxy-phenyl)-4,5-dimethyl-benzo[1,2-b;4,3-b']difuran.

Utility, Testing and Administration

General Utility

Compounds, compositions/formulations and methods of the present invention are useful in treating a number of disorders, particularly those characterized by oxidative stress and/or inflammation. In particular, compounds of the present invention can be used in the treatment of cerebral ischemia ("stroke"), myocardial ischemia (myocardial infarction and other forms of heart disease), diabetes, renal disease, pre-menstrual syndrome, asthma, cardiopulmonary inflammatory disorders, chronic heart failure, rheumatoid arthritis, muscle fatigue, intermittent claudication and for the preservation of allograft tissue for transplantation.

The compounds of the present invention have also shown use in reducing C-reactive protein (CRP) associated with inflammation and /or inflammatory conditions including cardiovascular diseases or disorders, such as atrial fibrillation, unstable angina, coronary artery disease, peripheral artery disease, cardiac allograft vasculopathy (CAVD), mastitits, preclampisia, inflammatory bowel conditions, stroke, tissue infarction, lumbosciatic, estrogen/progestin hormone replacement therapy (HRT); infection (bacterial, viral and protozoan), bacterial meningitis, trauma, surgery, biomaterial implants, smoking, obesity, neurodegenerative diseases such as Alzheimers, infectious disease such as for example myocarditis, cardio rhyopathy, acute endocarditis orpericarditis, aatherosclerosis, sustemic inflammatory response (SIRS)/sepsis, adult respirtoru distress syndrome (ARDS), asthma, rheumatoid arthritis, osteoarthritis, systemic lupus erythematosis, airway hyperresponsiveness (AHR), bronchial hyper-reactivity, chronic obstructive pulmonary disease (COPD), congestive heart failure (CHF), inflammatory complications of diapetes mellitus type I and II, metabolic syndrome, end stage reanl disease (ESRD), pre-menstrual syndrome (PMS) or muscle fatigue or inflammation, multiple organ dysfunction syndrome (MODS), airway hyper-responsiveness (AHR), bronchia hyper-reactivity, aging, acute allergic reactions, periodontal disease, such as gingivitis and dermal conditions including inflammatory skin conditions.

The compounds, formulations and methods of the present invention are useful in treating a number of dermatological conditions, including, but not limited to prevention and protecting skin tissue against age-related damage or damage resulting from insults such as harmful ultraviolet (UV) radiation, stress and fatigue. Such compounds, formulations and methods are likewise useful in hair care and treatments of the scalp, for example by incorporation in medicated shampoos, anhydrous hair conditioners and the like. Such compounds, formulations and methods are likewise useful in reduction of hair growth.

For example, exposure to sunlight can pose a number of hazards to the skin. The major short-term hazard of prolonged exposure to sunlight is erythema, i.e., sunburn, which primarily results from UVB radiation having a wavelength of from about 290 nm to about 320 nm. Over the long term, however, such prolonged exposure can often cause malignant changes in the skin surface to occur. Epidemiologic studies demonstrate a strong relationship between sunlight exposure and human skin cancer. Another long-term hazard of ultraviolet radiation is premature aging of the skin, which is primarily caused by UVA radiation having a wavelength of from about 320 nm to about 400 nm. This condition is characterized by wrinkling and pigment changes of the skin, along with other physical changes such as cracking, telangiectasis, solar dermatoses, ecchymoses, and loss of elasticity. Individuals, particularly those having light-skin who burn easily and tan poorly, who have had a great deal sun exposure in childhood can show the following gross cutaneous alterations in later adult life: wrinkling, leatheriness, yellowing, looseness, roughness, dryness, mottling (hyperpigmentation) and various premalignant growths (often subclinical). These cumulative effects of sunlight are often referred to as "photoaging". Although the anatomical degradation of the skin is most advanced in the elderly, the destructive effects of excessive sun exposure are already evident by the second decade. Serious microscopic alterations of the epidermis and dermis occur decades before these become clinically visible. Wrinkling, yellowing, leatheriness and loss of elasticity are very late changes.

The compositions of the present invention are useful for regulating body and/or head hair growth, particularly for the reduction of hair growth. The composition should be applied to the area of the body where it is desired to inhibit hair growth. Typically, the composition can be applied to the face, particularly to the beard area of the face, i.e., the cheek, neck, upper lip, and chin. The composition can also be applied to the legs, arms, torso and armpit. The compostion is particularly suitable for the treatment of hirsutism. In humans the composition should be applied onece or twice a day, or even more frequently, for at least three months to achieve a perceived reduction in hair growth.

Other skin conditions that may benefit from the methods of the present invention include, but are not limited to, diaper rash, a common form of contact dermatitis and irritation occurring in infants, as well as adults, who wear diapers. U.S. Pat. No. 6,211,186, incorporated herein by reference, describes possible etiologies and methods of treating this condition. It is generally thought that one or more fecal and lipolytic enzymes, as well as ammonia, bacteria, urine pH, overhydration and Candida albicans may be involved in the onset of skin irritation and inflammation associated with diaper rash. It is also likely that physiological responses of the skin to the irritants, such as production of cytokines by keratinocytes, contribute to the ensuing appearance of erythema, papules, scaling and ulceration characteristic of the condition. In addition, compositions and methods of the present invention may be useful in treating acne, a skin condition characterized by a profound inflammatory component, and irritation including retinoid iinduced irritation.

The compositions of the present invention are also useful for regulating skin condition, including visible and/or tactile discontinuities in skin (especially the skin surface; such discontinuities are generally undesired). Such discontinuities may be induced or caused by internal and/or external factors, and include the signs of skin aging described herein. Visible discontinuities include pigmentation disorders.

The compositions of the present invention are useful for regulating signs of skin aging, especially visible and/or tactile discontinuities in skin texture associated with aging. It is to be understood that the present invention is not to be limited to regulation of the "signs of skin aging" that arise due to the above-mentioned mechanisms associated with skin aging, but is intended to include regulation of such signs irrespective of their mechanism of origin.

Testing

This section describes how compositions incorporating compositions of the present invention are selected, using in vitro and/or in vivo animal models, for example, and used as therapeutic interventions in three exemplary indications, i.e., stroke, chronic heart failure and myocardial infarction.

Insults to the brain that disrupt its blood supply, as in ischemia, or its oxygen supply, as in hypoxia (low oxygen) or anoxia (no oxygen), rapidly cause neuronal imbalance leading to cell death (Flynn, C. J., et al., 1989, in G. Siegel et al., (Eds), *Basic Neurochemistry*, Raven Press, N.Y.). Investigations into the cellular and molecular mechanisms that lead to neuronal damage and inflammation associated with various types of brain ischemia can be carried out using in vitro model systems, such as primary cell cultures, that retain the metabolic characteristics of neurons in vivo. The use of such cell-based models has led to advances in identification of biochemical mechanisms leading to neuronal death in conditions such as anoxia, hypoglycemia, excitotoxicity, and exposure to reactive oxygen species. Neuronal cell lines such as the pheochromocytoma cell line, PC12, are also useful models for studying the effects of oxidative stress on the structure and function of neuron-specific proteins that are expressed in the cell lines. As many neuronal cell lines do not express all the properties of genuine neurons, primary neuronal cultures are now widely used as in vitro models in which to discern the processes that occur in intact brain.

In vitro models of ischemia approximate oxygen and glucose deprivation that mimic in vivo conditions, for example, by placing neuronal cultures into large anaerobic or hypoxic chambers and exchanging culture medium with de-oxygenated and defined ionic composition media. The toxic overstimulation of neuronal glutamcate receptors, especially N-methyl-D-aspartate (NMDA) receptors, contributes to hypoxic-ischemic neuronal injury (Choi, D. M., 1988, *Neuron* 1: 623–634), ischemic induction of reactive oxygen species (ROS) (Watson, B. D., et al.,1988, Ann NY Acad Sci., 59: 269–281), excessive calcium influx (Grotta, J. C., 1988, *Stroke* 19: 447454), arachidonic acid increase (Siesjo, B. K., 1981, *J. Cereb. Blood Flow Metab.* 1: 155–186) and DNA damage (MacManus, J. P., et al., 1993, *Neurosci. Lett.*, 164: 89–92), each causing a cascade of neurodegeneration.

Primary embryonic hippocampal neuronal cells are widely recognized as useful in models of neuronal function. The hippocampus is a source of a relatively homogenous population of neurons with well-characterized properties typical of central nervous system (CNS) neurons in general. Pyramidal neurons, the principal cell type in the hippocampus, have been estimated to account for 85% to 90% of the total neuronal population (Banker and Goslin, 1998, *Culturing Nerve Cells*, $2^{nd}$ edition. The MIT Press, Cambridge, Mass.). The hippocampus also exhibits a remarkable capacity for activity-dependent changes in synaptic function, such as long-term potentiation (Hawkins R D, Kandel E R, Siegelbaum S A. (1993) Learning to modulate transmitter release: themes and variations in synaptic plasticity [review], *Ann. Rev Neurosci.* 16:625–665.).

In experiments carried out in support of the present invention according to methods detailed in the Examples, anoxia/ischemia was induced in primary cultures of hippocampal neuronal cells, and compounds were tested for their ability to prevent cell death. Compounds found to have activity in such in vitro assays are then further tested in one or more animal models of cerebral ischemia ("stroke"), such as the middle cerebral artery occlusion (MCAO) model in rats.

Briefly, primary cultures of hippocampal neurons are used to test compounds for activity in neuronal protection. Hippocampal cultures are typically prepared from 18- to 19-day fetal rats. At this age, the generation of pyramidal neurons, which begins in the rat at about E15, is essentially complete. The brain tissue at this stage is relatively easy to dissociate, the meninges are removed readily, and the number of glial cells still is relatively modest (Park L C, Calingasan N.Y., Uchida K, Zhang H, Gibson G E. (2000) Metabolic impairment elicits brain cell type-selective changes in oxidative stress and cell death in culture. *J Neurochem* 74(1):1 14–124).

In order to evaluate the activity of compounds of the present invention, a test compound is assessed for its ability to protect cells against one or more standard stressors, including hypoxia, as detailed in the Examples. In general, desirable therapeutic compound candidates are effective in this model at concentrations less than about 1 mM and even more preferably, less than about 100 $\mu$M. By effective, it is meant that such compounds protect at least 20%, preferably 30%, more preferably 40% and even more preferably 50% or more of the cells tested from stressor-induced death. By way of example, compounds that are effective in providing protection over a concentration a range of about 1 to 1000 $\mu$M would be expected to provide neuroprotection in vivo. Since precise values may vary depending upon the specific conditions under which the neuroprotective cell assay is carried out, it is the intent of the present disclosure to provide the foregoing criteria as guidance in the form of a benchmark against which to compare subsequently tested compounds, rather than to provide absolute concentrations at which the compounds of the present invention are considered to be effective. Typically, compounds that are found to be neuroprotective in such in vitro cell systems are then further tested in an in vivo animal model of neuroprotection, such as the rat middle cerebral artery occlusion model described below, or other appropriate models such as are well known in the art.

Cerebral ischemic insults are modeled in animals by occluding vessels to, or within, the cranium (Molinari, G. F., 1986, in H.J.M. Barnett, et al., (Eds) *Stroke: Pathophysiology, Diagnosis and Management*, Vol. 1, Churchill Livingstone, NY). The rat middle cerebral artery occlusion (MCAO) model is one of the most widely used techniques to induce transient focal cerebral ischemia approximating cerebral ischemic damage in humans, e.g., those who suffer from a stroke. The middle cerebral artery used as the ischemic trigger in this model is the most affected vessel in human stroke. The model also entails a period of reperfusion, which typically occurs in human stroke victims. MCAO involving a two-hour occlusion has been found to produce the maximum size of cortical infarction obtainable without increased mortality at twenty-four hours.

Briefly, a nylon filament is implanted into the right carotid artery of the rat. To effect occlusion, the rat is anesthetized, and the filament is advanced into the internal carotid artery 18–20 mm from the point of bifurcation of internal and external arteries and a suture is tightly ligated around the filament for a period of two hours. Two hours post occlusion, animals are re-anesthetized, and the filament is removed, to allow reperfusion for the remainder of the experiment. Test drugs can be administered any time during this process—before, during or after occlusion, and can be administered by one or more of a variety of means, including but not limited to intracerebroventricular (ICV) infusion, intravenous (IV) infusion, intraperitoneal (IP) administration, as well as enteral administration (e.g., gavage). Animals are maintained normothermic during the experiment, as described in the Examples. At a pre-determined time following occlusion and reperfusion, animals are sacrificed and their brains are removed and processed for assessment of damage as measured by infarct volume. In general, compounds are considered to have activity in this model, if they provide a significant reduction in total infarct volume at a dose that is less than about 10 mg/kg, preferably less than 1 mg/kg, more preferably less than 100 µg/kg and even more preferably less than about 1 µg/kg, when administered ICV or IV. By significant reduction of total infarct volume is meant a reduction of at least 20%, preferably at least 30%, more preferably at least 40%, and even more preferably about 50%, compared to control values.

Further validation of efficacy in neuroprotection can be assessed in functional tests, such as the grip strength test or the rotorod test. Animals treated with compounds that show neuroprotection maintain their pre-MCAO grip strength values after MCAO, as compared to untreated animals, who showed a significant reduction in grip strength, indicating loss of sensorimotor function. Likewise, animals treated with compounds that show neuroprotection also maintained their pre-MCAO rotorod activity scores after MCAO, as compared to untreated animals, who showed a significant reduction in rotorod scores, indicating loss of sensorimotor function at higher brain levels.

Similarly, primary cultures of myocytes can be used to test compounds in vitro for ability to provide protection against heart damage, resulting for example from myocardial ischemia or congestive heart failure. Preparation of myocardiocytes from neonatal rats is described in the Examples. Such cells are typically used to study molecular models of myocardial ischemia (Webster, K A, Discher, D J & Bishopric, N H. 1995. J. Mol. Cell Cardiol. 27:453458; Camilleri, L, Moins, N, Papon, J, Maublant, J, Bailly, P, de Riberolles, C & Veyre, A. 1997. Cell Biol. & Toxicol. 13:435–444; Bielawska, A E, Shapiro, J P, Jiang, L, Melkonyan, H S, Piot, C, Wolfe, C L, Tomei, L D, Hannun, Y A & Umansky, S R. 1997. Am. J. Pathol. 151:1257–1263) and are therefore accepted as indicative of myoprotective activity. Exemplary stressor assays for this purpose are provided in the Examples. For example, cardiomyocytes in culture exhibit contractile ("beating") activity; each cardiomyocyte contraction is associated with a rise in intracellular calcium termed a "calcium transient". These calcium transients can be measured using Fluo-4, a fluorescent dye which exhibits large fluorescence intensity increases upon the binding of calcium. This assay is cell-based and tests the ability of potential cytoprotectant molecules to guard against ischemic damage and allow the cells to maintain their contractile function.

Further validation of compounds can be carried out in a whole organ assay, such as the isolated heart (Langendorff) model of cardiac function. Similarly, compounds can be further validated in additional animal models of disease (e.g., diabetes, renal failure, asthma, muscle fatigue, inflammation), such as are well known in the art.

This section describes how compositions incorporating compositions of the present invention are selected, using in vitro and in vivo animal models and used as therapeutic interventions in dermatological indications. A number of cell screening assays for mediators of inflammatory response are well known in the art. Such mediators include but are not limited to inflammatory cytokines, interleukin -1.beta., and tumor necrosis factor alpha (TNF.alpha.). Other molecules have been reported for use as markers of inflammation, including for example C-reactive protein (CRP), certain adhesion molecules, and proteins such as leukotriene, thromboxane and isoprostane.

In vitro evaluation of anti-inflammatory activity can be determined by well characterized assays such as the E-selectin (ELAM) production assay or the CRP assay exemplified in Example 9, and in vivo evaluation can be determined by the carrageenan-induced paw edema assay. The ELAM assay measures activity of test compounds in reducing espression of ELAM in acrivated endothelial cells. Briefly, endothelial cells are crivated by adding known acrivalors such as lipopolysaccharides, TNF, or IL-1.beta., alone or in some combination. Activated cells produce ELAM, which can be measure unsing, for example, an E-selectin monoclonal antibody-based ELISA assay. In studies carried out in support of the present invention, ELAM production was decreased. In vivo evaluation of anti-inflammatory activity as described in Example 10, can be determined by well characterized assay. (Gabor, M. *Mouse Ear Inflammation Models and their Pharmacological Appications*, 2000). Carrageenan-Induced Paw Edema is a model of inflammation, which causes time-dependent edema formation following carrageenan administration into the intraplantar survace of a rat paw. The application of arachidonic acid (AA) to the ears of mice produces immediate vasodilatation and erythema, followed by the abrupt development of edema, which is maximal at 40 to 60 min. The onset of edema coincides with the extravasations of protein and leukocytes. After one hour the edema wanes rapidly and the inflammatory cells leave the tissue so that at 6 hours the ears have returned to near normal. These assays, respectively, measure a test compounds ability to treat these inflammatory processes via systemic and topical routes of administration.

Cytoprotective activity for skin can be evaluated in cell culture using the Epiderm Skin Model (EPI-100) from the Mattek Corporation of Ashland, Mass., as dexcribed in Example 7. Cell cultures of neonatal foreskin are cultured in accordance with the manufacturer's directions, and are assayed for percent cellular viability by measuring the amount of 3-(4,5-dimethylthazol-2-yl)-2,5-diphenyltetrazolium bromide (MTT) dye taken up by the cells.

Activity with respect to hair growth inhibition is described in Example 8.

Administration

The compounds of Formula I are administered at a therapeutically effective dosage, e.g., a dosage sufficient to provide treatment for the disease states previously described. Administration of the compounds of the invention or the pharmaceutically acceptable salts thereof can be via any of the accepted modes of administration for agents that serve similar utilities.

While human dosage levels have yet to be optimized for the compounds of the invention, generally, a daily dose is from about 0.01 to 2.0 mg/kg of body weight, preferably about 0.1 to 1.5 mg/kg of body weight, and most preferably about 0.3 to 1.0 mg/kg of body weight. Thus, for administration to a 70 kg person, the dosage range would be about 0.7 to 140 mg per day, preferably about 7.0 to 105 mg per day, and most preferably about 21 to 70 mg per day. The amount of active compound administered will, of course, be dependent on the subject and disease state being treated, the severity of the affliction, the manner and schedule of administration and the judgment of the prescribing physician.

The compositions of the present invention are suitable for providing protection against the harmful effects of ultraviolet radiation, preferably in personal care products. More preferably, the compositions of the present invention are suitable for use as sunscreens to provide protection to human skin from the harmful effects of UV radiation, which include, but are not limited to, sunburn and premature aging of the skin. The present invention therefore also further relates to methods of protecting human skin from the harmful effects of UV radiation. Such methods generally involve attenuating or reducing the amount of UV radiation that reaches the skin's surface. In the case of the present invention, the methods of treatment for the harmful effects of ultraviolet radiation also include administration of a composition of the invention after the exposure to UV radiation has already taken place. To protect the skin from UV radiation, a safe and effective (photoprotective) amount of the composition is topically applied to the skin. "Topical application" refers to application of the present compositions by spreading, spraying, etc. onto the surface of the skin. The exact amount applied may vary depending on the level of UV protection desired. From about 0.5 mg of composition per square centimeter of skin to about 25 mg of composition per square centimeter of skin are typically applied.

Compounds and methods of the invention may be employed in any skin care application where decreased inflammatory response is desirable. For example, compounds and compositions of the invention may be incorporated into leave-on and rinse-off acne preparations, facial milks and conditioners, shower gels, foaming and non-foaming facial cleansers, cosmetics, hand and body lotions, leave-on moisturizers, cosmetic and cleaning wipes, salves for poison ivy, chicken pox, or pruritis, or the like. Generally, for dermal applications, topical administration is preferred; however, systemic administration, as described elsewhere herein, is also possible.

Compositions of the present invention may also be used in cosmetic compositions. Cosmetic compositions of the present invention are ideally suited for use in treating the skin and lips, especially in the form of a lipstick or lip balm for applying to the lips a permanent or semi-permanent color, ideally with a gloss or luster finish. The cosmetic compositions can also be used in treating the skin and/or lips with a skin care agent for protection against exposure to adverse weather, including the wind and rain, dry and/or hot environments, environmental pollutants (e.g., ozone, smoke, and the like), or exposure to excessive doses of sunlight. The compositions are also useful in providing sun protection, moisturizing and/or conditioning for the hair and skin, improved skin feel, regulating skin texture, reducing fine lines and wrinkles, reducing oily shine on hair or skin, skin lightening and reducing skin or hair odor.

The cosmetic compositions can accordingly be applied to the skin and/or lips in the traditional manner with or without a conventional holder or applicator to provide a decorative and/or protective film thereto.

In employing the compounds of this invention for treatment of the above conditions, any pharmaceutically acceptable mode of administration can be used. The compounds of formula I can be administered either alone or in combination with other pharmaceutically acceptable excipients, including solid, semi-solid, liquid or aerosol dosage forms, such as, for example, tablets, capsules, powders, liquids, suspensions, suppositories, aerosols or the like. The compounds of formula I can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages. The compositions will typically include a conventional pharmaceutical carrier or excipient and a compound of formula I or a pharmaceutically acceptable salt thereof. In addition, these compositions may include other medicinal agents, pharmaceutical agents, carriers, adjuvants, and the like, including, but not limited to anticoagulants, blood clot dissolvers, permeability enhancers and slow release formulations.

Generally, depending on the intended mode of administration, the pharmaceutically acceptable composition will contain about 0.1% to 90%, preferably about 0.5% to 50%, by weight of a compound or salt of formula I, the remainder being suitable pharmaceutical excipients, carriers, etc.

One preferred manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc. Actual methods of preparing such dosage forms are known, or will be apparent, to those skilled in this art; for example, see *Remington's Pharmaceutical Sciences*, Mack Publishing Company, Easton, Penn., 15th Edition, 1975. The composition or formulation to be administered will, in any event, contain a quantity of the active compound in an amount effective to alleviate the symptoms of the subject being treated.

Dosage forms or compositions containing active ingredient in the range of 0.005% to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like. Such compositions may contain 0.01%–95% active ingredient, preferably 0.1–50%.

For a solid dosage form, the solution or suspension, in for example propylene carbonate, vegetable oils or triglycerides, is preferably encapsulated in a gelatin capsule. Such diester solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. No. Re. 28,819 and U.S. Pat. No. 4,358,603.

The formulation can be administered in a single unit dosage form for continuous treatment or in a single unit dosage form ad libitum when relief of symptoms is specifically required. For example, the formulation may be administered as a bolus or as a continuous intravenous infusion after onset of symptoms of stroke, myocardial infarction or chronic heart failure.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc:

A more recently devised approach for parenteral administration employs the implantation of a slow-release or sustained-release system, such that a constant level of dosage is maintained. See, e.g., U.S. Pat. No. 3,710,795. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2–2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

Dermatologic formulations of the present invention typically comprise a cytoprotective derivative of any of Formula I and optionally, a polar solvent. Solvents suitable for use in the formulations of the present invention include any polar solvent capable of dissolving the cytoprotective derivative. Suitable polar solvents include: water; alcohols (such as ethanol, propyl alcohol, isopropyl alcohol, hexanol, and benzyl alcohol); polyols (such as propylene glycol, polypropylene glycol, butylene glycol, hexylene glycol, maltitol, sorbitol, and glycerine); and panthenol dissolved in glycerine, flavor oils and mixtures thereof. Mixtures of these solvents can also be used. Exemplary polar solvents are polyhydric alcohols and water. Examples of preferred solvents include glycerine, panthenol in glycerine, glycols such as propylene glycol and butylene glycol, polyethylene glycols, water and mixtures thereof. Additional preferred polar solvents for use are alcohols, glycerine, panthenol, propylene glycol, butylene glycol, hexylene glycol and mixtures thereof.

Typically, the formulations of the present invention will comprise from about 0.1% to about 80%, preferably from about 0.5% to about 60%, more preferably from about 1% to about 30% and most preferably from about 3% to about 18% polar solvent.

An emollient may also be added to the cosmetic/dermatological compositions of the present invention. The emollient component can comprise fats, oils, fatty alcohols, fatty acids and esters which aid application and adhesion, yield gloss and most importantly provide occlusive moisturization. Suitable emollients for use are isostearic acid derivatives, isopropyl palmitate, lanolin oil, diisopropyl dimerate, maleated soybean oil, octyl palmitate, isopropyl isostearate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, hydrogenated coco-glycerides, isononyl isononanoate, isotridecyl isononanoate, myristal myristate, triisocetyl citrate, cetyl alcohol, octyl dodecanol, oleyl alcohol, panthenol, lanolin alcohol, linoleic acid, linolenic acid, sucrose esters of fatty acids, octyl hydroxystearate and mixtures thereof. Examples of other suitable emollients can be found in the Cosmetic Bench Reference, pp. 1.19–1.22 (1996), incorporated herein by reference. Suitable emollients include polar emollient emulsifiers (such as linear or branched chained polyglycerol esters) and non-polar emollients. The emollient component typically comprises from about 1% to about 90%, preferably from about 10% to about 80%, more preferably from about 20% to about 70%, and most preferably from about 40% to about 60%, of the cosmetic composition.

By "polar emollient," as used herein, is meant any emollient emulsifier having at least one polar moiety and wherein the solubility (at 30 degrees C.) of the cytoprotective derivative compound in the polar emollient is greater than about 1.5%, preferably greater than about 2%, more preferably greater than about 3%. Suitable polar emollients include, but are not limited to, polyol ester and polyol ethers such as linear or branched chained polyglycerol esters and polyglycerol ethers. Nonlimiting examples of such emollients include PG3 diisostearate, polyglyceryl-2-sesquiisostearate, polyglyceryl-5-distearate, polyglyceryl-10-distearate, polyglyceryl-10-diisostearate, acetylated monoglycerides, glycerol esters, glycerol tricaprylate/caprate, glyceryl ricinoleate, glyceryl isostearate, glyceryl myristate, glyceryl linoleate, polyalkylene glycols such as PEG 600, monoglycerides, 2-monolaurin, sorbitan esters and mixtures thereof.

By "non-polar emollient," as used herein, means any emollient emulsifier possessing no permanent electric moments. Suitable non-polar emollients include, but are not limited to, esters and linear or branched chained hydrocarbons. Non-limiting examples of such emollients isononyl isononanoate, isopropyl isostearate, octyl hydroxystearate, diisopropyl dimerate, lanolin oil, octyl palmitate, isopropyl palmitate, pariffins, isoparrifins, acetylated lanolin, sucrose fatty acid esters, isopropyl myristate, isopropyl stearate, mineral oil, silicone oils, dimethicone, allantoin, isohexadecane, isododecane, petrolatum, and mixtures thereof. The solubility of the compound in polar or non-polar emollients is determined according to methods known in the art.

Suitable oils include esters, triglycerides, hydrocarbons and silicones. These can be a single material or a mixture of one or more materials. They will normally comprise from 0% to about 100%, preferably from about 5% to about 90%, and most preferably from about 70% to about 90% of the emollient component.

Oils that act as emollients also impart viscosity, tackiness, and drag properties to cosmetic compositions such as lipstick. Examples of suitable oils include caprylic triglycerides; capric triglyceride; isostearic triglyceride; adipic triglyceride; propylene glycol myristyl acetate; lanolin; lanolin oil; polybutene; isopropyl palmitate; isopropyl myristate; isopropyl isostearate; diethyl sebacate; diisopropyl adipate; tocopheryl acetate; tocopheryl linoleate; hexadecyl stearate; ethyl lactate; cetyl oleate; cetyl ricinoleate; oleyl alcohol; hexadecyl alcohol; octyl hyroxystearate; octyl dodecanol; wheat germ oil; hydrogenated vegetable oils; castor oil; petrolatum; modified lanolins; branched-chain hydrocarbons; alcohols and esters; corn oil; cottonseed oil; olive oil; palm kernel oil; rapeseed oil; safflower oil; jojoba oil; evening primrose oil; avocado oil mineral oil, sheabutter, octylpalmitate, maleated soybean oil, glycerol trioctanoate, diisopropyl dimerate, and volatile and non-volatile silicone oils including phenyl trimethicone.

Suitable oils for use herein are acetylglycerides, octanoates, and decanoates of alcohols and polyalcohols, such as those of glycol and glycerol, the ricinoleates of alcohols and polyalcohols such as cetyl ricinoleate, PG-3 diisostearate, polyglycerol ethers, polyglyerol esters, caprylic triglycerides, capric triglycerides, isostearic triglyceride, adipic triglyceride, phenyl trimethicone, lanolin oil, polybutene, isopropyl palmitate, isopropyl isostearate, cetyl ricinoleate, octyl dodecanol, oleyl alcohol, hydrogenated vegetable oils, castor oil, modified lanolins, octyl palmitate, lanolin oil, maleated soybean oil, cetyl ricinoleate, glyceryl trioctanoate, diisopropyl dimerate, synthetic lanolin derivatives and branched chain alcohols, sucrose esters of fatty acids, octyl hydroxystearate and mixtures thereof.

Preferably, the oils used are selected such that the majority (at least about 75%, preferably at least about 80% and most preferably at least about 99%) of the types of oils used have solubility parameters that do not differ by more than from about 1 to about 0.1, preferably from about 0.8 to about 0.1.

A surfactant may also be added to compositions of the invention, in order to confer beneficial cosmetic or application properties. Surfactants suitable for use are those which can form emulsions and/or association structures. Surfactant emulsifier can be from 0% to about 20% of the formulation, preferably from 0% to about 15% and most preferably from about 1% to about 10%. Examples of suitable emulsifiers can be found in U.S. Pat. No. 5,085,856 to Dunphy et al.; and U.S. Pat. No. 5,688,831 to El-Nokaly et al. Examples of other suitable emulsifiers can be found in Cosmetic Bench Reference, pp. 1.22, 1.24–1.26 (1996), all of which are incorporated herein by reference.

Also useful herein are surfactants that form association structures, preferably lamellar or hexagonal liquid crystals, at ambient temperature when mixed with a polar solvent. Ambient temperature/room temperature as used herein typically means about 20° C. Generally ambient temperature can range from about 18° C. to about 27° C., preferably from about 20° C. to about 25° C., depending on such variables as geographical location, i.e. sub-tropical vs. temperature regions. One of ordinary skill in art is readily able to determine if association structures form at ambient temperatures. The surfactants suitable for use generally have a Krafft point at or below about ambient temperature about 20° C. or generally at or below about 18° C. to about 27° C., preferably at or below from about 20° C. to about 25° C.

The definition of Krafft point is well known in the art and one of ordinary skill in the art can readily determine a surfactant's Krafft point. In general terms, Krafft point is the melting point of the hydrocarbon chains of the surfactants. It can also be expressed as the temperature at which the solubility of an association colloid in water suddenly increases because critical micelle concentration is exceeded and micelles form.

In preparing a sample combination of surfactant and polar solvent to demonstrate the ability to form association structures, the surfactant needs to be sufficiently soluble in the polar solvent such that an association structure can form at ambient temperature. One of ordinary skill in the art is capable of determining compatible interactions.

Any surfactant which forms association structures at ambient temperature and is suitable for use in cosmetics is suitable for use herein. Surfactants suitable for use in cosmetics do not present dermatological or toxicological problems. Anionic surfactants, nonionic surfactants, cationic surfactants, amphoteric surfactants and mixtures thereof are suitable for use. Preferably anionic surfactants, nonionic surfactants, cationic surfactants, amphoteric surfactants and mixtures thereof having a Krafft point at or below about ambient temperature are used. More preferably, nonionic surfactants, cationic surfactants, amphoteric surfactants and mixtures thereof having a Krafft point at or below about ambient temperature are used.

The surfactants can be used at levels from about 4% to about 97%, preferably from about 5% to about 95%, more preferably from about 20% to about 90% and most preferably from about 30% to about 70% of the association structure.

The cosmetic compositions of this invention can contain one or more materials, herein singly or collectively referred to as a "solidifying agent", that are effective to solidify the particular liquid base materials to be used in a cosmetic composition. (As used herein, the term "solidify" refers to the physical and/or chemical alteration of the liquid base material so as to form a solid or semi-solid at ambient conditions, i.e., to form a final composition that has a stable physical structure and can be deposited on the skin under normal use conditions.) As is appreciated by those skilled in the art, the selection of the particular solidifying agent for use in the cosmetic compositions will depend upon the particular type of composition desired, i.e., gel or wax-based, the desired rheology, the liquid base material used and the other materials to be used in the composition. The solidifying agent is preferably present at a concentration of from about 0 to about 90%, more preferably from about 1 to about 50%, even more preferably from about 5% to about 40%, most preferably from about 3% to about 20%.

The wax cosmetic stick embodiments of this invention preferably contain from about 5% to about 50% (by weight) of a waxy solidifying agent. By the term "waxy solidifying agent," as used herein, is meant a solidifying material having wax-like characteristics. Such waxy materials may also serve as emollients. Among the waxy materials useful herein are the high melting point waxes, i.e., having a melting point of from about 65° C. to about 125° C., such as beeswax, spermaceti, carnauba, baysberry, candelilla, montan, ozokerite, ceresin, paraffin, synthetic waxes such as Fisher-Tropsch waxes, microcrystalline wax, and mixtures thereof. Ceresin, ozokerite, white beeswax, synthetic waxes, and mixtures thereof, are among those useful herein are disclosed in U.S. Pat. No. 4,049,792, Elsnau, issued Sep. 20, 1977, herein incorporated by reference in its entirety). Low melting waxes, having a melting point of from about 37° C. to about 75° C., are preferred for use in the wax stick embodiments of this invention. Wax stick embodiments of this invention, which contain volatile silicone oils as a liquid base material, preferably contain from about 10% to about 35%, more preferably from about 10% to about 20% (by weight), of a low-melting wax. Such materials include fatty acids, fatty alcohols, fatty acid esters and fatty acid amides, having fatty chains of from about 8 to about 30 carbon atoms, and mixtures thereof. Preferred wax-like materials include cetyl alcohol, palmitic acid, stearyl alcohol, behenamide, sucrose esters of tallow fatty acids, mono and di-fatty acid esters of polyethylene glycol, and mixtures thereof. Stearyl alcohol, cetyl alcohol, and mixtures thereof, are particularly preferred. Additional fatty acids, fatty alcohols, and other wax-like materials useful in this invention are also well known in the art.

EXAMPLES

The following preparations and examples are given to enable those skilled in the art to more clearly understand and to practice the present invention. They should not be considered as limiting the scope of the invention, but merely as being illustrative and representative thereof.

General Characterization Methods

Nuclear Magnetic Resonance (NMR) spectra were recorded on a Bruker DTX 300 spectrometer using, in most cases, tetramethyl silane (TMS) as the internal reference. Mass spectra were obtained on an Agilent 1100 LC/MSD instrument using either electrospray ionization (positive or negative mode) (ESI) or atmospheric pressure chemical ionization (positive or negative mode) (APCI).

Example 1

Determination of Activity Utilizing-Neuronal Cell Stress Assay

A. Isolation and Culture of Primary Hippocampal Neuronal Cells

Materials
 Neurobasal/B27i: Neurobasal medium (Life Technologies, Rockville, MD) with 1×B27 supplement (Life Technologies), 0.5 µM L-glutamine, 25 µM L-glutamic acid, and 1×Penicillin/Streptomycin.
 Hank's Basic Salt Solution (HBSS, Ca/Mg-free) was prepared by preparing 1×Hanks CMF (Gibco) supplemented with HEPES (10 mM, pH 7.3), sodium bicarbonate (0.35%), 1×Penicillin/Streptomycin, and 1 mM pyruvate.
 Poly-D-lysine (Sigma, St. Louis, Mo.), 50 µg/ml solution filtered through 0.2 µm filter tubes.
 Sigmacote (Sigma, St. Louis, Mo.).
 Plastic Culture Flasks (T75 cm$^2$) or 12-well cell culture plates treated with Poly-D-Lysine (Sigma, St. Louis, Mo.).

Preparation of Primary Hippocampal Neuronal Cells

A pregnant female mouse (E18-E19) was euthanized with $CO_2$ prior to removal of the uterus, which was then placed in a sterile plastic petri dish. The embryos were removed from the sac, and the embryonic brains were removed and immersed in cold (4° C.) Buffered Salt Solution (HBSS; Ca/Mg free; Life Technologies) in a small petri dish. Hippocampi were then removed from the brains under a dissecting microscope and were placed on a paraffin-covered dish. The meninges were stripped away and the dissected hippocampi were collected in a small petri dish in HBSS. The hippocampi were transferred to a 15-ml centrifuge tube (normally 10–12 brains)filled with HBSS. The tube containing the brains was centrifuged at 1000 rpm for 2 min in a tabletop centrifuge. The supernatant was removed, 2 ml of HBSS was added to the hippocampi in the tube, and the resulting suspension was triturated 2 times each with long-tipped siliconized glass pipettes having progressively smaller apertures, starting with a pipette with a standard size opening (approximately 1.0 mm diameter), following with one having an aperture of half standard size (approximately 0.5 mm diameter), then with one having an aperture about one-half that size (0.25 mm diameter). The suspension was then centrifuged again at 1000 rpm for 2 min in a tabletop centrifuge, the supernatant was discarded, and 2 ml of Neurobasal/B27i (with antibiotics) was added to the tube. The trituration procedure described above was then repeated on this suspension.

The density of cells was determined on a small aliquot of cells using standard counting procedures and correcting for cell viability by trypan blue stain exclusion. Using this procedure, the expected yield is $3\times10^5$–$6\times10^5$ cells/brain. Cells were then added to PDL-coated 24-well plates,flasks or MetTek dishes in Neurobasal/B27I at a density of about $1.5\times10^6$ cells (T75 flask) or about 70,000 cells/well of a 24-well plate. Plated cells were incubated at 37 degrees in an atmosphere of 5% $CO_2$/95% $O_2$. Media was renewed after 3–4 days by replacing half of it with fresh Neurobasal/B27m medium, containing 5 µM cytosine arabinoside (AraC). Seven to eight days from the initial culture, the media was renewed again, by removing one-half or it and replacing with an equal amount of fresh Neurobasal/B27m medium (without Ara-C).

B. Hippocampal Anoxia-Reoxygenation Cell Death Assay

This assay was used to induce ischemia by anoxia-reoxygenation in cultured hippocampal neuronal cells. Test compounds were added to assess potency and efficacy against ischemia-induced neuronal cell injury and cell death.

Materials.
 Neurobasal media, NoG neurobasal media, B27 supplement and B27 Supplement minus AO were obtained from Invitrogen Life Technologies.
 Neurobasal/B27 medium was prepared with 2×B27 minus AO supplement, 0.5 mM L-glutamine and 0.25× penicillin/streptomycin.
 Cell Tracker Green was obtained from Molecular Probes and a fresh 5 µM solution was prepared from 10 mM stock just before use.

LoG-Neurobasal contains NoG neurobasal medium plus 1 mM glucose, 0.5 mM L-glutamine, 0.25×Penicillin/Streptomycin, and 10 mM Hepes (pH 7.4).

Primary hippocampal neuronal cells were prepared according to the methods described above and were cultured in poly-D-lysine coated 24-well plates for 10–11 days prior to use.

Deoxygenated LoG-Neurobasal medium (100 ml) was prepared by pre-equilibrating the medium in a T150 cm² flask in a hypoxic chamber overnight. Following pre-incubation under hypoxic conditions, the LoG-Neurobasal media was lightly bubbled with 100% $N_2$ for 30 min to completely deoxygenate the media. An additional 20 ml LoG-Neurobasal was pre-equilibrated in a T75 cm² flask and was incubated in a normal incubator (5% $CO_2$) overnight. Reoxygenated medium was prepared by placing Neurobasa/B27 media overnight in the culture incubator (5% $CO_2$/95% $O_2$).

10–11 Days after plating the hippocampal neurons, existing culture medium (Neurobasal/B27m) was removed from the cells by aspiration. Cells were washed once with 600 µl/well (24-well culture plates) of glucose free-BSS. Neurons were replenished with deoxygenated LoG-Neurobasal (400 µl per well for each well of a 24-well plate). Test compounds were added directly to each well (usually 3 concentrations of the compound plus positive control, each in triplicate). Most test compounds were dissolved in 100% DMSO; however, concentrations were adjusted such that the final concentration of DMSO in the cell media never exceeded 0.5%. Plates containing cells with test compounds were placed in a hypoxic chamber for 4–5 hr with plate lids ajar. For normoxia controls, pre-equilibrated normoxic LoG-Neurobasal medium was added to each well of cells, and the plate was replaced in the normal culture incubator for 4–5 hr. After 4–5 hr of hypoxia, the existing media was carefully aspirated off, and 400 µL of new, reoxygenated (pre-equilibrated) Neurobasal/B27 was added to each well. The same test compounds (in the same the concentrations) were added back into the corresponding wells. Plates were placed in the cell culture incubator (5% $CO_2$/95% $O_2$) and reoxygenated for 20–24 hr. After reoxygenation for 20–24 hr, live neurons were quantitated using the cell tracker green fluorescence method, described below.

To test for cell viability, existing culture medium was aspirated from each well of the 24 well plates, and neurons were washed once with 1 mL of HBSS (pH 7.4, pre-warmed to 30–37° C.). To each well was added 500 µL of 5 µM Cell Tracker Green fluorescent dye dissolved in HBSS. Plates were placed in the dark at room temperature for 15 minutes, then were washed with 1 mL of HBSS. 500 µL of HBSS was then added to each well, and fluorescent cells were counted using a fluorescent microscope. Significantly increased cell viability compared to control cells is indicative of a protective compound.

Certain compounds of the present invention when tested as described above provided protection against stressor-induced cell death in at least about 20% of the cells tested, at concentrations ranging from about 1 to 1000 µM.

Example 2

Myocyte Calcium—Contractility Assay

A. Isolation and Culture of Primary Neonate Myocytes

Materials
10×Heart Dissection Solution (HDS) contains the following components (g/l) in tissue grade water: NaCl, 68; HEPES, 47.6; $NaH_2PO_4$, 2; Glucose, 10; KCl, 4; $MgSO_4$, 1, pH adjusted to 7.4. Prior to filter sterilization of diluted (1×HDS) solution, 10 mg phenol red was added to each 500 milliliters of medium.

Transferrin and Bovine Insulin were obtained from Life Technologies, and resuspended at a concentration of 4 mg/ml in tissue culture grade water.

DMEM-F12-DMEM/F12, powder, 1:1 containing glutamine and pyridoxine hydrochloride was purchased from Life Technologies. To one liter equivalent of the powder was added 2.43 g of sodium bicarbonate and 10 ml of 100×Penicillin/Streptomycin in 950 ml of tissue culture grade water with stirring. The pH was adjusted to 7.2 with 1 M HCl and volume was adjusted to 1 liter. The solution was filter sterilized then 2.5 ml of 4 mg/ml Transferrin, 250 µl 4 mg/ml Insulin and 30.7 mg of bromodeoxyuridine were added.

DMEM-F12 was also prepared 4% FBS for pre-coating the tissue culture plates and initial suspension of the cardiomyocyte pellet.

Collagenase solution-49 mg of collagenase was resuspended in 120 ml 1×HDS.

Preparation of Primary Neonatal Myocyte Cultures

Tissue culture ware was pre-coated with DMEM-F12-4% FBS by incubating 50 µl per well of a 96-well plate and 0.25 ml per 12-well plate at 37° C.

Two-day old rat pups were removed from their mothers and placed in a sterile container. Pups were dipped quickly into 70% alcohol, then decapitated and the body was placed in an empty sterile tissue culture dish. An incision was made starting at the neck and progressing towards the belly, cutting through the sternum. The heart was removed and placed in a tissue culture dishes containing 1×HDS. The atria were trimmed, and the remaining ventricles were placed into a separate tissue culture dish containing 1×HDS, where they were sectioned into 3–4 pieces each. Ventricles were then transferred to a sterile 250 ml glass flask and the 1×HDS was removed. Twenty milliliters of pre-warmed collagenase solution were added to the ventricles, followed by incubation at 37° C. with shaking. After 30 minutes, the collagenase solution was removed and replaced with 20 ml fresh pre-warmed collagenase. Incubation was continued for an additional 30 minutes. At the end of the incubation, any tissue chunks were allowed to settle prior to removing the collagenase (containing the isolated cardiomyocytes) from the disrupted tissue pieces. The isolated myocytes were added to a 50 ml Falcon tube containing 2 ml Fetal Bovine Serum (FBS). The remaining tissue pieces were subjected to a second digestion by adding 20 ml fresh pre-warmed collagenase and incubating as above for 30 minutes. This second digest was then centrifuged at 1000 rpm for 10 minutes (tabletop centrifuge). The resulting supernatant was discarded, and the cell pellet was suspended with 4 ml FBS. The resulting cell suspension was placed in the incubator at 37° C. This step was repeated several additional times to harvest additional material.

Percoll gradients were prepared by adding 2.5 ml of 10×HDS to 22.5 ml of Percoll (Life Technologies) with mixing (Percoll Stock). Top Gradient solution (11 ml Percoll Stock and 14 ml 1×HDS) and Bottom Gradient solution (13 ml Percoll Stock and 7 ml 1×HDS) were prepared. Four milliliters of the Top Gradient solution were transferred into 6×15 ml sterile Falcon tubes. Three milliliters of the Bottom Gradient solution were placed in each tube by inserting a serological pipette to the bottom of the tube and slowly adding the liquid.

All the digests (5) were pooled in one 50 ml Falcon tube and centrifuged on a tabletop centrifuge at 1000 rpm for 10 minutes. The supernatant was discarded, and the cell pellet was resuspended in 12 ml of 1×HDS. Two milliliters of the cell suspension was added to the top of each gradient. The gradient tubes were then centrifuged at 3000 rpm for 30 minutes without braking in a Beckman Allegra 6 centrifuge (GH 3.8A rotor). Following centrifugation, the cells segregated into two sharp bands at the two interfaces. The lower band of the two bands was enriched for cardiomyocytes; there was also a cardiomyocyte pellet at the bottom of the tube. The upper band was enriched for fibroblasts and other non-cardiomyocytes. The upper portion of the gradient was aspirated down to just above the cardiomyocyte layer. The cardiomyocyte layer was then carefully removed along with the pellet, and the two fractions were pooled in a sterile 50 ml Falcon tube, along with corresponding fractions from additional gradient tube; then 1×HDS was added to a total volume of about 50 ml. The tube was centrifuged at 1000 rpm for 7 minutes. The supernatant was discarded and resuspended in 25 ml 1×HDS. A further 25 ml of 1×HDS was added and the centrifugation step was repeated. The cell pellet was resuspended carefully but thoroughly in 40–50 of DMEMF12-4% FBS.

A small aliquot of the cell suspension was counted in a hemocytometer. The DMEM/F12-FBS coating medium was aspirated from the tissue culture dishes. The cardiomyocytes were added to the dishes at a plating density of $7.5\times10^4$/well per 96-well in 200 μL and $1.5\times10^5$/well per 12-well in 3 ml. The cultures were incubated at 37° C. with 5% $CO_2$ overnight. The original medium was removed, and add fresh DMEM/F12-5% FBS was added to each culture, prior to incubation at 37° C. with 5% $CO_2$ for a further 48 hours, before use.

B. Contractility Assay
Materials
   Complete DMEM-F12: DMEM/F12, powder, 1:1 containing glutamine and pyridoxine hydrochloride was purchased from Life Technologies (Invitrogen Life Technologies, Carlsbad, Calif.). Powder sufficient to prepare one liter of buffer and 2.43 g of sodium bicarbonate was mixed into 950 ml of tissue culture grade water. The pH was adjusted to 7.2 with 1M HCl and the remaining water was added to make 1 liter. Following filter sterilization, 10 ml of 10×Penicillin/Streptomycin, 2.5 ml of 4 mg/ml Transferrin, 250 μl 4 mg/ml Insulin and 30.7 mg of bromodeoxyuridine were added, and the mixture was incubated at 37° C. prior to use.
   1 mM glucose in DMEM was made from DMEM without L-glutamine, without glucose, without sodium pyruvate, purchased from Life Technologies.
   20 μM Fluo-4: Cell permanent AM ester of Fluo-4 was obtained from Molecular Probes (Eugene, Oreg.) as a dry powder to be stored at −20° C. This fluorescent dye is light sensitive and should be made up fresh at 1 mM in DMSO prior to use to prevent light degradation.
   10 mM $CaCl_2$ solution was made fresh each day in 1×HBSS and incubated at 37° C. prior to use.
Neonatal cardiomyocytes were isolated as described above. The cardiomyocytes were plated in 96-well format (black clear-bottomed plates) at a density of $7.5\times10^4$ per well and grown for 2 days in the presence of 5% FBS prior to use in the assay.

Physiological ischemia was simulated by placing the cardiomyocytes in an anaerobic chamber (0% $O_2$, 85% $N_2$, 5% $CO_2$ & 10% $H_2$) in DMEM containing 1 mM glucose. Positive control cells are treated with DMEM-F12 containing 25 mM Glucose, which protects against the anoxia.

The test compounds were made up in DMEM-1 mM glucose in 96 deep-well mother plates and appropriately diluted for use in the assay. The media was removed from the cells and replaced with 200 μl of either DMEM-F12 or 1 mM DMEM with or without test compounds. The plates were then placed inside the 37° C. incubator in the anaerobic chamber and incubated for 16 hours. The plates were then removed and reoxygenated by the addition of DMEM-F12. The DMEM with or without test compounds is carefully removed from the cells and replaced with pre-warmed DMEM-F12 containing 5% FBS. Since the anoxic treatment may damage and/or kill the cells, causing them to dislodge from the bottom of the wells gentle aspiration of media is required at this step. The cells were then placed in a normal incubator at 37° C. and incubated for two hours to allow the cells to reoxygenate.

A working solution of 20 μM Fluo-4 was added to pre-warmed 1×HBSS. The cells were loaded with Fluo-4 by first removing media from the cells and replacing with 100 μl of 20 μM Fluo-4. Unloaded control cells were treated in parallel with 1×HBSS alone. All cells-were then incubated at 37° C. for 30 minutes. Before fluorescence measurements were made, the cells were washed in indicator-free medium (HBSS) to remove any dye that is non-specifically associated with the cell surface. Cells were then incubated for an additional 20 minutes at room temperature. Basal Fluo-4 fluorescence was measured using the 485 nm excitation and 538 nm emission filter pair on a microplate flourometer (Fluorskan™, Thermo Labsystems Oy, Helsinki, Finland). Each well was read for 160 ms to obtain a baseline reading, then stimulated to contract by addition of 10 mM $CaCl_2$. Following incubation at 37° C. for 30 minutes, a stimulated fluorescence was taken after 90 minutes.

Compounds of the present invention such as
   (5-Hydroxy-3,6,7-trimethyl-benzofuran-2-yl)-phenyl-methanone;
   Acetic acid 6,7-dimethyl-2-(2-morpholin-1-yl-acetyl)-benzofuran-5-yl ester;
   2-(1-Hydroxy-2-morpholin-4-yl-ethyl)-6,7-dimethyl-benzofuran-5-ol;
   Acetic acid 2-(2-bromo-acetyl)-6,7-dimethyl-benzofuran-5-yl ester;
   1-(5-Hydroxy-6,7-dimethyl-benzofuran-2-yl)-2-morpholin-4-yl-ethanone;
   1-(4-Bromo-5-hydroxy-6,7-dimethyl-benzofuran-2-yl)-ethanone;
   1-(5-Hydroxy-6,7-dimethyl-benzofuran-2-yl)-ethanone;
   4-(5-Hydroxy-6,7-dimethyl-benzofuran-2-yl)-benzonitrile;
   5-Hydroxy-6,7-dimethyl-benzofuran-2-carbaldehyde;
   2-Hydroxymethyl-6,7-dimethyl-benzofuran-5-ol;
   5-Hydroxy-6,7-dimethyl-benzofuran-2-carboxylic acid methyl ester;
   5-Hydroxy-6,7-dimethyl-benzofuran-2-carboxylic acid;
   5-Hydroxy-6,7-dimethyl-benzofuran-2-carboxylic acid bis-(2-hydroxy-ethyl)-amide;
   5-Hydroxy-6,7-dimethyl-benzofuran-2-carboxylic acid 2-[2-(2-methoxy-ethoxy)-ethoxy]-ethyl ester; and
   5-Hydroxy-6,7-dimethyl-benzofuran-2-carboxylic acid bis-(2-hydroxy-ethyl)-amide;
   when tested as described above show a protection of at least 20% and the presence of calcium transients in amounts indicative of ability guard against ischemic damage and allow the cells to maintain their contractile function.

Example 3

Rat Middle Cerebral Artery Occlusion (MCAO) Model of Cerebral Ischemia

A. Animal Preparation

Male Wistar rats (Harlan, Ind.) weighing 300–350 g are commonly used in these experiments. Animals are allowed free access to water and commercial rodent diet under standard laboratory conditions. Room temperature is maintained at 20–23° C. and room illumination is on a 12/12-hour light/dark cycle. Animals are acclimatized to the laboratory environment 5 to 7 days prior to the study, and fasted (with free access to water) overnight before surgery.

B. Middle Cerebral Artery Occlusion (MCAO)

Anesthesia is maintained by inhalation of 3.0% isoflurane (Aerrane, Front Dodge, Iowa) in 0.8% oxygen. The animal's neck was shaved and sterilized before operation. Body temperatures were controlled and maintained at 37.5° C.+/−1 degree via external heating and cooling devices. To lower the body temperature, animals are placed in a cooling chamber, which uses ice to cool circulating air. Throughout the study the body temperature is recorded using a temperature transponder (BMDS Inc., Seaford, Del.) implanted subcutaneously at the time of MCAO between the rat shoulder blades that allows the user to read the body temperature via a pocket scanner (BMDS Inc., Seaford, Del.). The body temperature may also be taken by inserting the temperature probe into the animal's rectum. Body temperature is recorded every hour for 6 hours post-occlusion; however, body temperatures were taken more frequently so that they could be maintained at the normothermic temperature.

Animals were subjected to two hours MCAO using a modified intraluminal filament technique, as follows: A midline incision on the ventral part of the neck is made to expose external and internal carotid arteries. The right external and common carotid arteries are ligated by a suture (silk 5/0, Carlisle Laboratories, Farmers Branch, Tex.) and the right internal artery is temporarily ligated using a microvascular clip (Fine Science Tool Inc., Foster City, Calif.). A small incision was made in the common carotid artery. A nylon filament, its tip rounded by heating, is prepared from a fishing line (Stren Fishing Lines, Wilmington, Del.) and is inserted from the right common carotid artery. The filament is advanced into the internal carotid artery 18–20 mm from the point of bifurcation of internal and external arteries and a suture is tightly ligated around the filament. Two hours post occlusion, animals are re-anesthetized to allow reperfusion for the remaining of the experiment by removal of the filament.

C. Drug Administration

Test compounds may be administered by any of a number of routes, such as those described below. Compounds can be administered before, during or after occlusion, as appropriate to the protocol.

a) Intracerebroventricular (ICV) Infusion

The anesthetized animal is placed on a stereotaxic apparatus (Harvard Apparatus, S. Natick, Mass.). Anesthesia is maintained by inhalation of 3.0% isoflurane (Aerrane, Front Dodge, Iowa) in 0.8% oxygen throughout the entire procedure. The scalp is shaved and sterilized prior to surgery. A midline sagittal incision about 3 cm long is made slightly behind the eyes to expose the skull. The skull is scraped with a rounded end spatula to remove periosteal connective tissue. A bur hole is placed 1.5 mm lateral, 1 mm posterior to the left of the bregma to mark the left lateral ventricle. A brain infusion cannula (ALZET Co., Palo Alto, Calif.) is inserted 4 mm deep into the hole. The desired depth is adjusted by attaching spacers to the cannula. The cannula attached to a 4-cm silastic catheter (Helix Medical Inc., Carpinteria, Calif.) fixed in place with dental cement (Ketac-cement, Norristown, Pa.). The catheter is either attached to a primed osmotic pump placed subcutaneously between the shoulder blades for permanent infusion or to a syringe for a short infusion.

b) Intravenous (IV) Osmotic Pump Implantation Into the Jugular Vein

Anesthesia is maintained by inhalation of 3.0% isoflurane (Aerrane, Front Dodge, Iowa) in 0.8% oxygen throughout the entire procedure. The animal's neck will be shaved and sterilized before operation. A midline incision is made on the ventral part of the neck to exposes the jugular vein. The vein is isolated and ligated with a suture (silk 5/0, Carlisle Laboratories, Farmers Branch, Tex.) rostral to the point of the incision and a microvascular clip (Fine Science Tool Inc., Foster City, Calif.) close to the heart. A small incision is made between two ligations. A 2-cm silastic catheter (Helix Medical Inc.) attached to a PE-60 tube (Becton. Dickinson and Co. Sparks, Md.) connected to an ALZET (ALZET CO. Palo Alto, Calif.) pump is introduced and advanced 2 mm into the jugular vein toward the heart. The microvascular clip is removed and the catheter is secured in place with a suture (silk 5/0, Carlisle Laboratories, Farmers Branch, Tex.). The pump is placed into a pocket made subcutaneously between the shoulder blades, allowing the catheter to reach over neck to the jugular vein with sufficient slack to permit free movement of neck and head.

c) IV Infusion via Femoral Vein

Anesthesia is maintained by inhalation of 3.0% isoflurane (Aerrane, Front Dodge, Iowa) in 0.8% oxygen throughout the entire procedure. The exterior site of the right femoral vein is shaved and sterilized prior to surgery. A 3-cm incision is made in the right groin region and the femoral vein is isolated. A small incision is made on the femoral vein temporarily ligated with a microvascular clip to introduce and advance a polyethylene (PE-50) catheter (Becton Dickinson and Co. Sparks, Md.). The catheter is secured in place with suture (silk 5/0, Carlisle Laboratories, Farmers Branch, Tex.). The other end of the catheter is attached to a syringe filled with the heparinized saline for the bolus injection. Using a hemostat, a pocket is made subcutaneously on the back of the animal so the PE catheter can be brought up to the exteriorization point at the nape of the neck for either a bolus injection or a continuous injection by an osmotic pump.

d) Intraperitoneal (IP) Injection

An awake rat is held in a standard hand hold position, a 23¾ G needle is injected into the lower right quarter of the abdomen pass the peritoneum, slightly off the midline. To avoid organ injection, the plunger of the syringe is slightly pulled back. If no fluid is withdrawn, the content of the syringe is delivered into the abdominal cavity.

D. Behavioral Assessment

One hour after MCAO, the animal was gently held by its tail and observed for forelimb flexion. Then the animal is placed on the floor to be observed for walking pattern; only the animals that score 3 on Bederson grading system (Table 1) are included in the study.

TABLE 1

Bederson Grading System for Neurological Evaluation

| Neurological deficit | Grading | Behavioral observation |
|---|---|---|
| Normal | grade 0: | No observable deficit |
| Moderate | grade 1: | forelimb flexion |
| Severe | grade 2: | forelimb flexion, decreased resistance to lateral push |
|  | grade 3: | forelimb flexion, decreased resistance to lateral push, circle to paretic side |

E. Evaluation of Ischemic Damage

Twenty-four hours post-MCAO, or longer, in some experiments, animals were sacrificed by $CO_2$ asphyxiation (dry ice). The brain was quickly removed from the skull, using standard procedures, rinsed in chilled saline solution, and placed on a rat brain tissue slicer (ASI instrument, MI). Seven 2-mm thick coronal slices are cut from each brain using razor blades. The slices were immersed in 0.9% saline containing 1.0% 2,3,5-triphenyltetrazolume chloride (TTC) (Sigma Chemical Co., St. Louis, Mo.) and incubated in a 37° C. water bath for 30 minutes.

After staining, each 2-mm slice is photographed with a TMC-7 camera (JH Technologies, Calif.) which is directly connected to a desktop PC to capture and save the image of each brain slice. This image is used for the measurements of the regions of interest using a computer-based image processing system (Metamorph).

To measure each area, the region of interest is selected using a freehand selection tool, the area is automatically computed by selecting the measure command. The measurements for primary regions of interest are right hemisphere, left hemisphere, total infarct, subcortical infarct, total penumbra and subcortical penumbra. After all regions of interest are measured for all seven slices of the brain, they are sorted by slice number and the corresponding regions of interest using an Excell macro called statistic final. This macro also calculates the cortical penumbra, cortical infarct and total ischemic damage for each slice; the corresponding areas of each rat brain will be added together to produce a single measurement for each area. Since the ipsilateral hemisphere is swollen following MCAO, edema volume is calculated and reported as the volumetric differences between the right and left hemispheres of each brain slice. Using the % of hemispheric swelling all the volumes will be corrected for the edema. The volume of the damage is determined using the calculations below for each rat's brain.

| Measurement | Equation | Corrected Value(s) |
|---|---|---|
| Cortical Penumbra (C.P.) | Total Penumbra − Subcortical Penumbra | Total Penumbra (T.P.$_{corr}$) = (T.P. × % H.S./100)<br>C.P.$_{corr}$ = C.P. − (C.P. × % H.S./100)<br>S.P.$_{corr}$ = S.P. − (S.P. × % H.S./100) |
| Cortical Infarct | Total Infarct − Subcortical Infarct | T.I.$_{corr}$ = T.I. − (T.I. × % H.S./100)<br>S.I.$_{corr}$ = S.I. − (S.I. × % H.S./100)<br>C.I.$_{corr}$ = C.I. − (C.I. × % H.S./100) |
| Total Ischemic Damage (T.I.D.) | Total Penumbra + Total Infarct | T.I.D.$_{corr}$ = T.I.D. − (T.I.D. × % H.S./100) |
| Total Volume ($mm^3$) | Each value is multiplied by 2 (the thickness of the tissue). | |
| Edema Volume | The volumetric differences between the sum of right and left hemispheres determines the edema volume. | |
| % Hemispheric swelling (H.S.) | Edema × 100/ left hemisphere | |

F. Statistical Analysis

Sample size is chosen to achieve a 90% probability of significant results. The measurements, which represented the same region of interest in seven slices of each rat's brain are added together to yield a single measurement for total infarct, subcortical infarct, cortical infarct, total penumbra, subcortical penumbra, cortical penumbra, total ischemic damage and edema in each animal. Group data are presented as means +/−SEM. Differences at the level of $p<0.05$ are considered statistically significant. Between groups comparison of each region of interest are carried out by unpaired student t test (between two groups) or one way ANOVA followed by post hoc Bonferroni's multiple comparisons or by the nonparametric Dunnett's test (between control and the drug treated groups).

Compounds of the present invention can be tested as described above.

Example 4

Model of Myocardial Infarction: Left Coronary Ligation (Rat)

Male Sprague-Dawley weighing 250–320 g were allowed free access to water and commercial rodent diet under standard laboratory conditions. Room temperature was maintained at 20–23° C. and room illumination was on a 12/12-hour light/dark cycle. Animals were acclimatized to the laboratory environment 5 to 7 days prior to the study and were fasted overnight prior to surgery.

Surgical Procedure for Acute Studies: Rats were anaesthetized with Urethane (1.2–1.5 gm/kg). Core body temperature was maintained at 37° C. by using a heating blanket. The surgical area was shaved, and a ventral midline incision was made to expose the trachea and jugular area. A catheter (PE50) was placed in the jugular for administration of compound and maintenance anesthesia. The trachea was incised and a 14–16-gauge modified intravenous catheter was inserted and tied in place as an endotracheal tube. The animal was placed in right lateral recumbency and initially placed on a Harvard ventilator with a tidal volume of 5–10 ml/kg. 100% $O_2$ was delivered to the animals by the ventilator. ECG electrodes were placed to record a standard Lead II ECG. The surgical site was cleaned with alcohol swab, and a skin incision was made over rib cage over the $4^{th}$–$5^{th}$ intercostal space. The underlying muscles were dissected with care to avoid the lateral thoracic vein, to expose the intercostal muscles. The chest cavity was entered through $4^{th}$–$5^{th}$ intercostal space, and the incision expanded to allow visualization of the heart. The pericardium was opened to expose the heart. A 6–0 silk suture with a taper needle was passed around the left coronary artery near its origin, which lies in contact with the left margin of the pulmonary cone, at about 1 mm from the insertion of the left auricular appendage. A piece of tubing was placed over the suture to form an occluder. The coronary artery was occluded for 30 minutes by sliding the tube towards the heart until resistance is felt and holding it in place with a vascular clamp. The ECG was monitored for S-T changes indicative of ischemia. After 30 minutes, the occluder was removed, leaving the suture in place. The ECG was monitored for the first 10 minutes of reperfusion. The rat was transferred to the pressure control ventilator for the remainder of the protocol. The rats were ventilated by a small animal ventilator with a peak inspiratory pressure of 10–15 cm $H_2O$ and respiratory rate 60–110 breaths/min. The heart was allowed to reperfuse for 90 minutes.

Surgical procedure for 24 hour study: Rats were anaesthetized with Ketamine/Xylazine IP (95 and 5 mg/kg) and intubated with a 14–16-gauge modified intravenous catheter. Anesthesia level was checked every 15 minutes by toe pinch. Core body temperature was maintained at 37° C. by using a heating blanket. The surgical area was shaved and scrubbed. A ventral midline incision was made to expose the jugular vein. A catheter (PE50) was placed in the jugular for administration of compound and maintenance anesthesia. The animal was placed in right lateral recumbency and initially placed on a ventilator with a tidal volume of 5–10 ml/kg $H_2O$ or a pressure controlled ventilator with a peak inspiratory pressure of 8–15 cm $H_2O$ and respiratory rate 60–110 breaths/min. 100% $O_2$ was delivered to the animals by the ventilator. ECG electrodes were placed to record a standard Lead II ECG. The surgical site was cleaned with surgical scrub and alcohol. A skin incision was made over rib cage over the $4^{th}$–$5^{th}$ intercostal space. The underlying muscles were dissected with care to avoid the lateral thoracic vein, to expose the intercostal muscles. The chest cavity was entered through $4^{th}$–$5^{th}$ intercostal space, and the incision expanded to allow visualization of the heart. The pericardium was opened to expose the heart. A 6–0 silk suture with a taper needle was passed around the left coronary artery near its origin, which lies in contact with the left margin of the pulmonary cone, at about 1 mm from the insertion of the left auricular appendage. A piece of tubing was placed over the suture to form an occluder. The coronary artery was occluded for 30 minutes by sliding the tube towards the heart until resistance is felt and holding it in place with a vascular clamp. The ECG was monitored for S-T changes indicative of ischemia. After 30 minutes, the occluder was removed, leaving the suture in place. The ECG was monitored for the first 10 minutes of reperfusion. The incision was closed in three layers. The IV catheter was removed or tunneled under the skin and exteriorized between the shoulder blades to allow for blood withdrawal or further drug therapy. The rat was ventilated until they are able to ventilate on their own. The rats were extubated and recovered on a heating pad. Once awake, they were returned to their cage(s). Animals may receive Buprenorphine (0.01–0.05 mg/kg SQ) for post-operative analgesia. After the designated reperfusion time (24 hours) the animals were anesthetized and the hearts removed under deep anesthesia.
Treatment Protocols Diet Animals were fed a custom diet prior to or after coronary ligation. The length of treatment varies with the study. Doses were calculated based on the average consumption of 15 gms of feed per day for a 300 gm rat. Rat weights were monitored during the study. Feed not consumed was weighed to estimate consumption rates.

IV treatment: A ventral incision was made to expose the jugular area. A catheter (PE50) was placed in the jugular vein for administration of compound. Animals were dosed by bolus injection and/or continuous infusion. The time and duration of treatment varies with the protocol.

Tissue Processing

After reperfusion, each animal received 200 units of heparin IV under general anesthesia and the heart was removed and placed in cold saline. After removal the coronary artery was ligated with the suture that is already in place. The heart was placed on a perfusion apparatus and Evans Blue dyed was infused delineate the area at risk. The heart was then cut into five 2-mm thick transverse slices from apex to base. The slices were incubated in 1% triphenyltetrazolium chloride (TTC) in 0.9% saline for 20 minutes at 37° C. Tetrazolium reacts with NADH in the presence of dehydrogenase enzymes causing viable tissue to stain a deep red color and that is easily distinguished from the infarcted pale-unstained necrotic tissue. The slices were placed apex side down in the lid of a small petri dish for the staining procedure. The bottom of the dish was placed over the slices to keep them flat. The slices were photographed in order from apex to base, with the base side up. The areas of infarcted tissue, area at risk and the whole left ventricle were determined using a computerized image analysis system. The total area for each region was added together to give a total for the entire heart. Infarct size was expressed both as a percentage of the total ventricle and the area at risk.
Statistical Analysis Group data is represented as means +/–SEM. Comparisons between treatment groups were made using ANOVA with $p<0.05$ considered significant. Post hoc comparisons may be made using either Dunnett's test or Tukey's test .

The compounds of the present invention can be tested by this method.

Example 5

Evaluations of Sensorimotor Behavior

A. Fore and Hindlimb Grip Strength Test in Rats

Animals with cerebral infarction induced by transient or permanent unilateral occlusion of the middle cerebral artery (MCA) and sham-operated rats are tested for grip strength, a standard model of neuromuscular function and sensorimotor integration, using a Computerized Grip Strength Meter for Rats (Dual Stand Model, Columbus Instruments, Columbus, Ohio).

Animals are moved into the testing room for 30 minutes before testing. Prior to testing, each gauge is calibrated with a set of known weights and the apparatus is adjusted for the size of animal, according to manufacturer's instructions. The forelimb measurements are carried out with the meter in the tension peak mode to freeze the reading as the subject is pulled away from the grip bar. The hindlimb measurements are carried out with the meter in the compression peak mode to freeze the reading as the subject's hindlimbs are pulled over the bar toward the meter. Each animal is hand-held by the investigator while pulled past the grip bars, using a consistent technique, leaving the fore and hind limbs free to grasp the grip bars.

Testing is carried out on postoperative day 2 and repeated, in a blind-randomized fashion, twice weekly for a defined interval. Typically, three successive readings are taken for each animal with an intertrial interval long enough to record the data and zero both meters for the next trail.

B. Rota-Rod Test in Rats

Apparatus: Rota-Rod Treadmill for Rats (7750 Accelerating Model, from UGO BASILE, COMERIO-ITALY).

Procedure: Animals with cerebral infarction induced by transient or permanent unilateral occlusion of the middle cerebral artery (MCA) and sham-operated rats are tested in this study, using a Rota-Rod Treadmill for Rats (7750 Accelerating Model; UGO Basile, Comerio, Italy). The animals are moved into the testing room 30 minutes before testing. Every rat receives 2–3 training runs of 1–2 minutes at intervals of 2–3 hours before testing. The cylinder on the apparatus is set in motion before placing the rats in position. The motor is set at a constant selected speed in 7700 on RESET mode, and the rats are placed, one by one, in their sections.

Testing is carried out on postoperative day 2 and repeated, in a blind-randomized fashion, twice weekly for a defined interval. Typically, three successive readings are taken for each animal with an intertrial interval long enough to record the data and zero both meters for the next trail.

Example 6

Model of Congestive Heart Failure

Experimental Preparation

225–275 g male Sprague-Dawley rats are anaesthetized with ketamine/xylazine (95 mg/kg and 5 mg/kg) and intubated with a 14–16-gauge modified intravenous catheter. Core body temperature is maintained at 37° C. by using a heating blanket. The surgical area is clipped and scrubbed, and the animal is placed in right lateral recumbency and initially placed on a ventilator with a peak inspiratory pressure of 10–15 cm $H_2O$ and respiratory rate 60–110 breaths/min. 100% $O_2$ is delivered to the animals by the ventilator. ECG electrodes are positioned to record a standard Lead II ECG. An incision is made over rib cage over the 4th–5th intercostal space. The underlying muscles are dissected with care to avoid the lateral thoracic vein, to expose the intercostal muscles. The chest cavity is entered through 4th–5th intercostal space, and the incision expanded to allow visualization of the heart. The pericardium is opened to expose the heart.

A 6-0 silk suture with a taper needle is passed around the left coronary artery near its origin, about 1 mm from the insertion of the left auricular appendage. The coronary artery is occluded by tying the suture around the artery. The ECG is monitored for S-T changes indicative of ischemia. If the animal develops ventricular fibrillation, gentle cardiac massage is used to convert the animal to a normal rhythm. Sham operated controls are subjected to the same procedure, but the suture is not tied off. The incision is closed in three layers. Infected or moribund animals are eliminated from the study.

Four weeks after surgery, the animals are anesthetized, and a catheter is placed in the right carotid artery and advanced into the left ventricle for hemodynamic measurements. Pressure traces are recorded and analyzed for heart rate, left ventricular systolic and diastolic pressure, left ventricular developed pressure, and dP/dt max and min. After measurements are taken, 2 ml blood is removed and placed in serum and plasma tubes. The heart is removed and placed on a Langendorff apparatus as follows:

Langendorff Procedure

Buffer preparation: Krebs-Henseleit (KH) buffer solution containing NaCl 118 mmol/L, KCl 4.7 mmol/L, $MgSO_4$ 1.2 mmol/L, $KHPO_4$ 1.2 mmol/L, Glucose 11 mmol/L, $NaHCO_3$ 25 mmol/L and $CaCl_2$ 2.5 mmol/L (Sigma) is made fresh daily using Nanopure pyrogen-free water.

The animal receive 200 units of heparin, the thorax is opened and the heart is rapidly excised and placed in ice-cold KH buffer solution. After the contractile activity of the heart completely ceases, the heart is trimmed and the ascending aorta freed from the connective tissue. The heart is quickly weighed, then the aorta is cannulated, and the heart mounted on a non-recirculation Langendorff perfusion apparatus (Radnoti Glass Technology, Inc., Monrovia, Calif.). The heart is perfused in a retrograde fashion via the aorta with KH buffer solution oxygenated with 95% $O_2$ and 5% $CO_2$ to maintain pH 7.4 at 37° C. To assess contractile function, a latex balloon is inserted into the left ventricle through the mitral orifice and connected to a pressure transducer by rigid polyethylene tubing. The balloon is inflated with water to a left ventricular end-diastolic pressure (LVEDP) of 1 to 10 mm Hg. Flow is initiated at 12 ml/min and adjusted during the first 15 minutes of baseline to obtain a perfusion pressure between 65 and 75 mmHg. Target parameters for baseline are as follows:

Perfusion pressure 65–75 mmHg
LVEDP 10 mmHg

The heart is allowed to stabilize for 15 minutes. After this time functional measurements are taken, after which a pressure volume curve is generated by adjusting the volume in the balloon in 0.05 ml increments and recording ventricular pressures. The left ventricular systolic pressure (LVSP), left ventricular end diastolic pressure (LVEDP), left ventricular developed pressure (LVDP), first derivative of the rise and fall in the left ventricular pressure (dp/dt max, dp/dt min), perfusion pressure and heart rate are automatically recorded using a computerized data acquisition system.

Other Measurements

After removal the heart, lungs and liver are weighed. The lungs and liver are weighed and dried overnight for determination of wet to dry ratios.

After completing the Langendorff procedure, the heart is placed in cold saline to stop the beating, then cut into five 2-mm thick transverse slices from apex to base. Slice #3 will be incubated in 1% triphenyltetrazolium chloride (TTC) in 0.9% saline for 20 minutes at 37° C. Tetrazolium reacts with NADH in the presence of dehydrogenase enzymes causing viable tissue to stain a deep red color and that is easily distinguished from the infarcted pale-unstained necrotic tissue. The slice is placed apex side down in the lid of a small petri dish for the staining procedure. The bottom of the dish is placed over the slice to keep it flat. The slice is then photographed and the areas of infarcted tissue, left and right ventricle are determined using a computerized image analysis system. Infarct size is expressed as a percentage of the total ventricle. Total areas of the left and right ventricle are measured. The remaining sections are divided into right and left ventricle and frozen for TBARS and glutathione assays.

Treatment Protocol

No treatment is given to the sham operated and control groups.

Measurements for CHF Study

In vivo measurements are made of heart rate (HR), left ventricular systolic pressure (LVSP), left ventricular end diastolic pressure (LVEDP), dP/dt min and max, right ventricular systolic pressure (RVSP), right ventricular diastolic pressure (RVDP), and right ventricular end diastolic pressure (RVEDP), as well as total body weight. Ex vivo measurements are made of HR, LVSP, LVEDP, dP/dt min and max, and pressure volume curve. Also measured ex vivo are heart weight, infarct size, Glutathione peroxidase (GPX), catalase, catalase, thiobarbituric reactive substances (TBARS), glutathione ratio (GSH/GSSG), lung and liver wet to dry weight ratios, serum isoprostane and interleukin-6 (IL-6).

Certain compounds of the present invention can be tested by this method.

Example 7

Skin Protection Assay

Cytoprotective activity for skin can be evaluated in cell culture using the Epiderm Skin Model (EPI-100) from the Mattek Corporation of Ashland, Mass. Cell cultures of neonatal foreskin are cultured in accordance with the manufacturer's directions, and are assayed for percent cellular viability by measuring the amount of 3-(4,5-dimethylthazol-2-yl)-2,5-diphenyltetrazolium bromide (MTT) dye taken up by the cells. Viable cells take up this dye and convert it to insoluble formazin crystals that resides in the mitochondria of the cells until extracted with alcohol. The amount of MTT converted to extractable formazin crystals is directly proportional to the viability of the cell culture. MTT is measured spectrophotometrically.

Cells are exposed to UV light at a rate of 1.5 Minimal Erythemal Dose (MED) per hour per square centimeter, for a total dose of about 31.5 $mJ/cm^2$, from a solar simulator (filtered to yield wavelengths in the region of 290–400 nm) in the presence of the cytoprotective compound or mixtures thereof to measure the effect of test compounds to protect the cell culture from the generation of free radicals resulting from the ultraviolet light.

The controls for this study are cell cultures without added test compound (positive control). All cell cultures are also compared to cultures that are not exposed to UV light and do not include the cytoprotective agents or blends in order to determine percent cellular viability (negative control). This latter measurement is assumed to be equal to 100% viability.

Cell cultures treated with the cytoprotective compounds of the invention show greater survival than do positive control cell cultures, when tested as described above.

Example 8

Hair Growth Inhibition

Reduction of hair growth is demonstrated when the frequency of hair removal is reduce, or the subject perceives less hair on the treated site, or quantitatively when the weight of hair removed by shaving (i.e., hair mass) is reduced. Male intact Golden Syrian hamsters are considered acceptable models for human beard growth in that they display oval shaped flank organs, one on each side, each about 8 mm. in major diameter, which grow thick black and coarse hair similar to human beard hair. The organs produce hair in response to androgens in the hamster.

To evaluate the effectiveness of a particular inhibitor in reducing hair growth, the flank organs of each of a group of hamster are depilated by applying a thioglycolate based chemical depilatory (Surgex). To one organ of each animal 10 µL of vehicle alone once a day is applied, while to the other organ of each animal an equal amount of vehicle containing the inhibitor is applied. After thirteen applications (one application per day for five days a week) the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

Compounds of this invention can be tested in this assay.

Example 9

In vitro Cellular Inflammation Assay

A Human Hep3B Cells—CRP Assay

Hep3B Cell Line is obtained from the American Type Culture Collection (ATCC Catalog No. HB-8064). The Hep3B cell line was derived from liver tissue of an 8-year-old Black male. The cells are epithelial in morphology and produce tumors in nude mice. The cells produce α-fetoprotein, hepatitis B surface antigen, albumin, α-2-macroglobulin, α-1-antitrypsin, transferrin, plasminogen, complement C3 and β-lipoprotein (Knowles BB, et al., Science, 1980, 209:497–499). This cell line has been widely used to study hepatocyte cytokine and acute phase protein release (e.g., Damtew B, et al.,1993, J Immunol 150:4001–4007).

HEP3B cells are grown in Minimum Essential Medium (MEM; GIBCO) supplemented with 10% Fetal Bovine Serum (FBS; Hyclone), 1×Penicillin/Streptomycin (GIBCO, Cat #15140-122) and 0.1 mM non-essential amino acids (GIBCO, Catalog No. 11140-050). Cells are thawed and transferred to warm medium according to standard methods known in the art.

Cells are incubated in flasks at 37° C. with 5% $CO_2$ in an air atmosphere incubator. HEP3B growth media is changed every 2 days until the cells reach 70–80% confluence (approx. 3–4 days). For assay, the cells are transferred to 96-well plates, seeded at 5000 cells per well in culture media, and left to grow for 7 days in a 37° C. incubator (air supplemented with 5% $CO_2$). Media is replaced daily until assay. Test compounds are diluted into "Stimulus Buffer" (MEM medium containing 0.1 mM non-essential amino acids, 1×penicillin/streptomycin, 10% FBS with 10 ng/ml IL-1β, 20 ng/ml IL-6 and 1 µM dexamethasone. Media is removed from the cells and is replaced with 200 µl of test dilution. Cells are returned to the incubator for three days at 37° C. CRP ELISA is then performed on supernatant from the cells, as described below.

Costar EIA/RIA plates are coated with rabbit anti-human CRP (DAKO) diluted 1:4000 in carbonate buffer (100 µl/well) for 45 minutes at 37° C. Plates are then washed 5×with CRP washing buffer (50 mM Tris-HCl, 0.3M NaCl, 0.5 Ml Tween-20, pH 8.0) using an automatic plate washer. Plates may be dried, covered and refrigerated until use. Supernatant (100 µl) is removed from each well of the test plates and added to the corresponding well of a precoated ELISA plate.

100 µl HRP-conjugated rabbit anti-human CRP (DAKO) diluted 1:500 (in CRP wash buffer) is added to each well, followed by incubation for 30 minutes at 37° C. Plates are washed 5× with CRP washing buffer using the automatic plate washer. 200 µl of 3,3',5,5'-Tetramethyl Benzidine (TMB) liquid Substrate System (Sigma, St. Louis, Mo.) is added to each well, followed by incubation in the dark for 15 minutes at room temperature. Finally, 50 µl of 1 M $H_2SO_4$ is added to each well and absorbance at 450 nm is immediately measured in a microtiter spectrophotometer.

CRP measured as above is normalized to cell count per well, using a cell viability assay, such as the Cell Tracker Green assay. To do this, the remainder of the medium is from the cell test plates, cells are washed with 200 µl of pre-warmed 1×Hanks Basic Salt Solution (HBSS; GIBCO), and 100 µL of 5 µM Cell Tracker Green (Molecular Probes, Eugene, Oreg.) is added to each well. Plates are then incubated at 37° C. for 30 minutes. Cells are then washed twice with prewarmed 1×HBSS. Plates are immediately read using a Fluoroskan® flourometer with a 485 excitation/538 emission filter pair.

In a CRP assay such as the one disclosed herein, compounds such as:

6,7-Dimethyl-3-phenyl-benzofuran-5-ol;

1-(4-Bromo-5-hydroxy-6,7-dimethyl-benzofuran-2-yl)-ethanone;

1-(5-Hydroxy-6,7-dimethyl-benzofuran-2-yl)-2-morpholin-4-yl-ethanone;

Acetic acid 2-(6-hydroxy-3-methyl-[1,3]oxazinan-6-yl)-6,7-dimethyl-benzofuran-5-yl ester;

1-(5-Hydroxy-6,7-dimethyl-benzofuran-2-yl)-ethanone;

3-(4-Methoxy-phenyl)-6,7-dimethyl-benzofuran-5-ol;

4,5-Dimethyl-1,8-diphenyl-benzo[1,2-b;4,3-b']difuran; and 1,8-Bis-(4-fluoro-phenyl)-4,5-dimethyl-benzo[1,2-b;4,3-b']difuran;

at an $EC_{50}$ of between about 10 to about 40 micromolar were effective at reducing CRP levels.

B. Cell-ELAM

Endothelial-Leukocyte Adhesion Molecule (ELAM), also known as E-selectin, is expressed on the surface of endothelial cells. In this assay, lipopolysaccharide (LPS) and IL-1p are used to stimulate the expression of ELAM; test agents are tested for their abilities to reduce this expression, in accordance with studies showing that reduction of leukocyte adhesion to endothelial cell surface is associated with decreased cellular damage (e.g., Takada, M., Et al., Transplantation 64: 1520–25, 1997, Steinberg, J. B., et al., J. Heart Lung Trans. 13:306–313, 1994).

Endothelial cells may be selected from any of a number of sources and cultured according to methods known in the art; including, for example, coronary artery endothelial cells, human brain microvascular endothelial cells (HBMEC; Hess, D. C., et al., Neurosci. Lett. 213(1): 37–40, 1996), or lung endothelial cells. Cells are conveniently cultured in 96-well plates. Cells are stimulated by adding a solution to each well containing 10 µg/ml LPS and 100 µg/ml IL-1β for 6 hours in the presence of test agent (specific concentrations and time may be adjusted depending on the cell type). Treatment buffer is removed and replaced with pre-warmed Fixing Solution® (100 µl/well) for 25 minutes at room temperature. Cells are then washed 3×, then incubated with Blocking Buffer (PBS+2% FBS) for 25 minutes at room temperature. Blocking Buffer containing Monoclonal E-Selectin Antibody (1:750, Sigma Catalog #S-9555) is added to each well. Plates are sealed and stored at 4-overnight. Plates are washed 4× with 160 µL Blocking Buffer per well. Second Antibody-HRP diluted 1:5000 in Blocking Buffer is then added (100 µL/well), and plates are incubated at room temperature (protected from light) for two hours. Plates are then washed 4× with Blocking Buffer before addition of 100 µL of ABTS Substrate solution at room temperature (Zymed, Catalog #00-2024). Wells are allowed to develop for 35 minutes, before measurement at 402 nm in a Fluoroskan® Reader with shake program for 10 seconds. Positive results are recorded as a decrease in ELAM concentration in tested wells, as compared to control wells.

In an ELAM assay, such as the one described herein, certain compounds of the present invention at $EC_{50}$ in a range of 10–1000 micromolar, and in particular in a range of 200–600 micromolar, were able to reduce the expression of ELAM.

C. Interleukin-1.beta. Microglial Celll Assay

Materials And Equipment

A. Materials For Cell Preparation And Experiment

Mouse microgial cell line

DMEM High Glucose media (Gibco Catalog #11965-092)

FBS (Hyclone Catalog #SH30070.03)

100×Penicillin/Streptomycin (Gibco Catalog #15140-122).

LPS (Sigma Catalog #L2537)

Interferon-gamma(Sigma Catalog #I4777)

Cell Tracker Green (Molecular Probes Catalog #C2925)

HBSS buffer (950 ml Pyrogen-free water, 2.44 g/L MgCl2.6H20, 3.73 g/L KCl, 59.58 g/L Hepes, 58.44 g/L NaCl, 1.36 g/L KH2PO4, 1.91 g/L CaCl2 .2H2O and pH to 4.5 with HCl)

Sterile 96-well plates precoated with poly-D-lysine (Corning Catalog #3665)

96-well deep well mother plate, DyNA Block 1000 (VWR Catalog #40002-008)

B. Materials For Il-1beta Elisa

Mouse IL-1 beta Duo Set (R & D Systems Catalog #DY401)

Substrate Solution (R & D Systems Catalog #DY 999)

Bovine Serum Albumin fraction V (BSA V) (Sigma Catalog #A4503)

96-well Costar EIA high binding plates (VWR Catalog #29442-302)

Plate seal (VWR Catalog #29442-310)

PBS (Irvine Scientific Catalog #9240)

Cell Culture Grade Water (Irvine Scientific Catalog #9312)

Tween 20 (Sigma Catalog #P 1379)

Sucrose (Sigma Catalog #S7903)

Sodium Azide (Sigma Catalog #S 8032)

$H_2SO_4$ 5N (VWR Catalog #JT 5691-2)

Experimental Preparation and Procedure

Mouse IL-1beta Elisa:

Solutions: Wash Buffer: PBS 1L+500 µl Tween 20 (final 0.05%) pH 7.2–7.4. Blocking Buffer: 500 ml PBS+5 g BSA V (1%)+25 g Sucrose (5%)+0.25 g Sodium Azide (0.05%). Reagent Diluent: 500 ml PBS+5 g BSA V (1%) pH 7.2–7.4 and filter sterilize through 0.2 µm. Stop Solution: Make 2N sulfuric acid by adding 10 ml 5N $H_2SO_4$ to 15 ml of dd $H_2O$.

Duo Set Preparations:
1. The IL-1.beta. capture antibody was reconstituted in 1 ml of PBS to give a final concentration of 720 µg/ml, and the working concentration was 4 µg/ml. For coating one 96-well plate (at 100 µl/well) 56 µl of the 720 µg/ml stock was diluted into 10 ml of PBS.
2. The IL-1.beta.standards were reconstituted in 0.5 ml of Reagent Diluent (70 ng/ml). For a high standard of 1 ng/ml (2wells at 100 μl each+enough for series dilution) 7.1 μl of the 70 ng/ml standard were diluted into 0.5 ml of Reagent Diluent 3. The IL-1.beta. detection antibody was reconstituted in 1 ml of Reagent Diluent to give a final concentration of 18 μg/ml and the working concentration is 100 ng/ml. For one 96-well-plate (at 100 μl/well) 56 μl of the 18 μg/ml stock was diluted into 10 ml of Reagent Diluent.

IL-1.beta ELISA Procedure:

Plate Preparation:

1. The Costar EIA Hi-binding plate was coated with capture antibody at 4 μg/ml. 56 μl of 720 μg/ml stock was taken for one plate and added to 10 ml of PBS. Each well was coated with 100 μl, and the plate was sealed and incubated overnight at room temperature.
2. Each well was aspirated and washed 3× with Wash Buffer. Each well was filled to the top, dispensed, and any remaining buffer was removed by inverting the plate and gently blotting against clean paper towels.
3. Non-specific binding sites were blocked by adding 300 μl of Blocking Buffer to each well, and after sealing, incubating for at least 1 hour at room temperature.
4. After washing the plate was now ready for the samples.

Assay Procedure:

5. 100 μl of either standard or sample were added in each well of the capture-coated and pre-blocked plate. The plate was sealed and incubated for 2 hours at room temperature, followed with washing as in step 2.
6. 100 μl of the detection antibody (100 ng/ml) were added to each well. For one 96-well plate 56 μl of the 18 μg/ml stock were diluted into 10 ml of Reagent Diluent.
7. The plate was sealed and incubated at room temperature for 2 hours., followed with washing as in step 2.
8. 100 μl of the working dilution of Streptavidin-HRP was added, and the plate was sealed and incubated in the dark for 20 minutes at room temperature, followed with washing as in Step 2.
9. The fresh Substrate Solution was prepared by mixing Color Reagent A ($H_2O_2$) and Color Reagent B (Tetramethylbenzidine) in a 1:1 ratio. 100 μl of this Substrate Solution mixture was added to each well and the plate was incubated in the dark for 20 minutes at room temperature.
10. 50 μl of Stop Solution was added to each well, mixing was ensured by gently tapping.
11. Each plate was read with the Spectramax once at 450 nm. If wavelength correction is available set to 540 or 570 nm.

Compounds of the present invention can be tested tested for their ability to reduce inflammation in this model.

Example 10

In vivo Cellular Inflammation Assay

These assays measure the ability of test compounds to prevent or reduce inflammation secondary to oxazolone or arachidonic acid.

A. Arachidonic Acid

Albino male CD-1 mice, 7–9 weeks old were used in this test. A 20% (w/v) arachidonic acid solution in acetone is prepared. Twenty microliters of the arachidonic acid solution is applied to the dorsal left ear of the mouse. Immediately thereafter, test compounds (20 μL in 70% ethanol/30% propylene glycol) are applied to the left ear. The untreated right ears served as control. Mice are sacrificed by $CO_2$ inhalation, one hour after treatment. The left and right ears are removed and 7 mm punch biopsies taken from each. The punch biopsies are weighed, and the differences calculated.

B. Oxazolone

CD-1 mice are induced by applying 3% oxazolone (Sigma) (30 mg/ml prepared in corn oil:acetone) to the shaved abdomen. Five days later, the mice are challenged with 2% oxazolone (20 mg/ml) in acetone on the left ear (right ear was untreated control). One hour after challenge, test compounds are applied to the left ear in 70% ethanol/ 30% propylene glycol. Animals are sacrificed 24 hours later and 7 mm ear punches are removed. The ear punches are placed on a balance scale, and the difference between the untreated and treated ears is determined. Percent inhibition is calculated by comparing the means of each group to the vehicle group. (Hydrocortisone serves as a positive control in this test.).

Compounds of the present invention can be tested for their ability to reduce inflammation in this model.

Example 11

6,7-Dimethyl-3-phenyl-benzofuran-5-ol

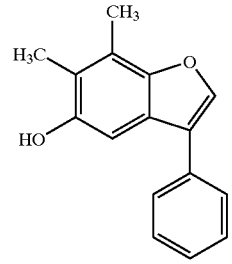

A mixture of 2,3-dimethyl-1,4-dihydroquinone (1.08 g, 7.826 mmol), 2-bromoacetophenone (1.45 g, 7.29 mmol), and potassium carbonate (1.78 g, 12.90 mmol) in acetone (30 mL) was stirred at room temperature for 3 h. The mixture was then poured into water resulting in the formation of a precipitate. The precipitate was washed with water and hexane, and dried to yield a mixture of mono and bis products. Purification by silica gel column eluting with 30% EtAOc in hexane, 2-(4-Hydroxy-2,3-dimethyl-phenoxy)-1-phenyl-ethanone (0.65 g) and 2-[2,3-Dimethyl-4-(2-oxo-2-phenyl-ethoxy)-phenoxy]-1-phenyl-ethanone (0.5 g).

Step 2:

A mixture of 2-(4-hydroxy-2,3-dimethyl-phenoxy)-1-phenyl-ethanone (1.2 g, 4.70 mmol) and polyphosphoric acid (ca. 100 mg) in xylene (10 mL) was stirred at 150° C. for 5 h. The mixture was poured into water, extracted with ethylacetate, washed and dried to give 6,7-dimethyl-3-phenyl-benzofuran-5-ol (560 mg) as a light brown solid. $^1$H NMR (CDCl$_3$, 300 MHz) δ: 7.71 (s, 1H), 7.60–7.20 (m, 5H), 7.06 (s, 1H), 4.76 (s, 1H, OH), 2.47, 2.29 (2s, 6H) ppm. $^{13}$C NMR (CDCl3, 75 MHz), δ: 150.43, 150.30, 141.15, 132.58, 129.00, 127.32, 123.48, 122.13, 121.31, 120.59, 102.25, 12.31, 11.95 ppm. MS (m/z): 239 (M+H$^+$).

Similarly by following the procedure described above but replacing bromoacetophenone with the appropriate substituted bromoacetophenones the following compounds were obtained:

3-(4-Fluoro-phenyl)-6,7-dimethyl-benzofuran-5-ol; $^1$H NMR (CDCl$_3$, 300 MHz) δ: 7.65 (m, 1H), 750 (m, 2H), 7.10–6.95 (m, 3H), 4.90 (s, 1H, OH), 2.44, 2.31 (2s, 6H) ppm. $^{13}$C NMR (CDCl$_3$, 75 MHz) δ: 163.79, 160.53, 150.37, 150.30, 140.97, 128.90, 128.79, 128.56, 128.52, 123.44, 121.41, 121.24, 120.78, 116.06, 115.78, 102.04, 12.30, 11.96 ppm. $^{19}$F NMR (CDCl$_3$, 300 MHz, TFA as reference) δ: −115.31 ppm. MS (m/z): 257 (M+H$^+$).

3-(4-Methoxy-phenyl)-6,7-dimethyl-benzofuran-5-ol $^1$H NMR (CDCl$_3$, 300 MHz) δ: 7.64 (s, 1H), 7.50 (dd, J=2.1, 6.7 Hz, 2H, 2H), 7.00 (m, 3H), 4.83 (s, 1H, OH), 3.84 (s, 3H), 2.46, 2.28 (2s, 6H) ppm. $^{13}$C NMR (CDCl$_3$, 75 MHz) 6: 158.92, 150.33, 150.23, 140.52, 128.47, 125.02, 123.69, 121.70, 121.25, 120.49, 114.45, 102.20, 55.47, 12.30, 11.95 ppm. MS (m/z): 269 (M+H$^+$).

3-(4-Chlorophenyl)-6,7-dimethyl-benzofuran-5-ol; ). $^1$H NMR (CDCl$_3$, 300 MHz) δ: 7.72 (s, 1H), 7.53 (d, J=8.6 Hz, 2H), 7.42 (d, J=8.6 Hz, 2H), 7.02 (s, 1H), 4.86 (s, 1H, OH), 2.47, 2.30 (2s, 6H) ppm. $^{13}$C NMR (CDCl$_3$, 75 MHz) δ: 150.41, 141.25, 133.04, 131.06, 129.17, 128.49, 123.17, 121.45, 121.12, 120.79, 101.99, 12.30, 11.94 ppm. MS (m/z): 273, 275 (M+H$^+$).

Example 12

4,5-Dimethyl-1,8-diphenyl-benzo[1,2-b;4,3-b'] difuran

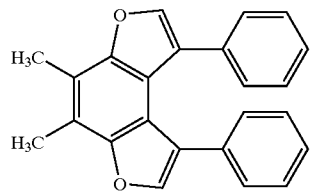

A mixture of 2-[2,3-Dimethyl-4-(2-oxo-2-phenyl-ethoxy)-phenoxy]-1-phenyl-ethanone (480 mg, 1.28 mmol) synthesized as described in Example 11, an excess of bromoacetophenone, and polyphosphoric acid (PPA, 100 mg) in xylene (10 mL) was stirred at 150° C. for 10 h. The mixture was then poured into water, extracted with EtOAc, the organic layer was washed with water and brine, dried over MgSO$_4$ and concentrated. The residue was purified by silica gel column eluting with 10–20% EtOAc in hexane to give 190 mg of 4,5-dimethyl-1,8-diphenyl-benzo[1,2-b;4,3-b']difuran (250 mg). $^1$H NMR (CDCl$_3$, 300 MHz) δ: 7.60 (s, 2H), 7.05 (m, 4H), 6.90 (m, 2H), 6.85 (m, 4H), 2.60 (s, 6H) ppm. $^{13}$C NMR (CDCl$_3$, 75 MHz) δ: 152.57, 141.48, 133.19, 128.42, 127.52, 126.87, 124.05, 117.40, 116.29, 11.80 ppm. MS (m/z): 339 (M+H$^+$).

Similarly by following the procedure of Example 12, the following compounds were obtained:

1,8-Bis-(4-fluoro-phenyl)4,5-dimethyl-benzo[1,2-b;4,3-b']difuran; $^1$H NMR (CDCl$_3$, 300 MHz) δ: 7.56 (s, 2H), 7.05 (m, 4H), 6.60 (m, 4H), 2.60 (s, 6H) ppm. $^{13}$C NMR (CDCl$_3$, 75 MHz) δ: 163.91, 160.66, 152.51, 141.44, 130.18, 129.16, 129.12, 122.77, 117.59, 116.27, 114.65, 114.36, 11.78 ppm. $^{19}$F NMR (CDCl$_3$, 300 MHz, TFA as reference) δ: −116.57 ppm. MS (m/z): 375 (MH$^+$).

1,8-Bis-(4-methoxy-phenyl)-4,5-dimethyl-benzo[1,2-b;4,3-b']difuran; ). $^1$H NMR (CDCl$_3$, 300 MHz) δ: 7.56 (s, 2H), 6.95 (d, J=8.7 Hz, 4H), 6.90 (m, 2H), 6.43 (d, J=8.7 Hz, 4H), 3.75 (s, 6H), 2.60 (s, 6H) ppm. $^{13}$C NMR (CDCl$_3$, 75 MHz) 6:158.49, 152.39, 141.07, 129.78, 125.51, 123.5, 117.24, 116.74, 112.98, 54.94, 11.78 ppm. MS (m/z): 399 (M+H$^+$).

Example 13

(5-Hydroxy-3,6,7-trimethyl-benzofuran-2-yl)-phenyl-methanone

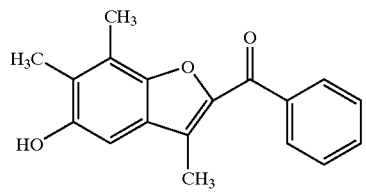

Step 1:

To a suspension of 2,3-dimethyl-1,4-dihydroquinone (11.58 g) and triethylamine (25 mL) in dichloromethane (100 mL) was slowly added acetic anhydride (16 mL). Then the mixture was stirred at room temperature for 2 h until the solid was dissolved. The mixture was washed with water, dried over MgSO4, and concentrated to dryness to give a solid. The solid was washed with hexane and ether to give 15.40 g of the 1,4 diacetate derivative of the starting material.

Step 2:

A suspension of the diacetate from Step 1 (5.08 g) in boron trifluoride acetic acid complex (15 mL) was stirred at 110° C. for 1 h. After cooling, the mixture was poured into ice, and the mixture was extracted with dichloromethane. The organic layer was washed with water and dried. After evaporation, the residue was recrystallized from EtOAc-hexane to give 4.37 g of 1-(2-hydroxy-5-acetoxy-3,4-dimethyl-phenyl)-ethanone.

Step 3:

The phenylethanone of Step 2 (500 mg) was dissolved in MeOH (20 mL), and potassium carbonate (1 eq.) was added followed by water (1 mL). The mixture was stirred at room temperature for 1 h, and then was poured into water. The solution was acidified with HCl and a precipitate was formed. The precipitate was collected and air dried to give about 350 mg of 1-(2,5-dihydroxy-3,4-dimethyl-phenyl)-ethanone.

Step 4:

1-(2,5-Dihydroxy-3,4-dimethyl-phenyl)-ethanone of Step 3 (275 mg) was dissolved in dichloromethane (20 mL) and 3,4-dihydro-2H-pyran (0.2 mL) was added followed by pyridinium p-toluenesulfonate (PPTS) (30 mg). The mixture was stirred at room temperature for 4 h. The mixture was dried over MgSO$_4$ and purified on silica gel column eluting with 30% EtOAc in hexane to give 397 mg of 1-[2-hydroxy-3,4-dimethyl-5-(tetrahydro-pyran-2-yloxy)-phenyl]-ethanone as a yellow solid.

Step 5

A mixture of the tetrahydropyran ether from Step 4 (250 mg), 2-bromo-1-phenyl-ethanone (250 mg), and potassium carbonate (300 mg) in DMF was stirred at room temperature for 3 h. The mixture was poured into water and extracted with ethyl acetate, the organic layer was dried and evaporated. Purification on a silica gel column eluting with 30% EtOAc in hexane gave 260 mg of a colorless solid which was then dissolved in DMF followed by the addition of cesium carbonate (2 eq.). The mixture was stirred overnight at room temperature, then poured into water and extracted with ethylacetate, the organic layer was dried and evaporated. The crude product was dissolved in MeOH with dil. HCl and stirred for 1 h. It was then poured into water and extracted with ethylacetate, the organic layer was washed, dried and evaporated. Purification on a silica gel column eluting with 30% EtOAc in hexane gave (5-hydroxy-3,6,7-trimethyl-benzofuran-2-yl)-phenyl-methanone (187 mg). $^1$H NMR (CDCl3 with MeOH-d4, 300 MHz) δ: 8.10 (m, 2H), 7.50 (m, 3H), 6.88 (s, 1H), 2.55, 2.43, 2.30 (3s, 9H) ppm. $^{13}$C NMR (CDCl$_3$ with MeOH-d4, 75 MHz) δ: 186.58, 152.26, 149.41, 148.23, 138.47, 132.81, 130.08, 128.61, 128.38, 127.37, 126.55, 121.64, 101.68, 101.63, 12.72, 12.51, 10.53 ppm. MS: 281 (M+H$^+$).

Example 14

1-(5-Hydroxy-6,7-dimethyl-benzofuran-2-yl) ethanone

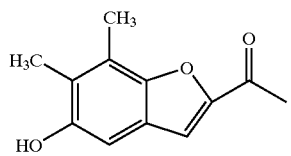

A mixture of 1-[6,7-dimethyl-5-(tetrahydro-pyran-2-yloxy)-benzofuran-2-yl]-ethanone (1.1 g) (prepared from 2,5-dihydroxy-3,4-dimethyl-benzaldehyde following the procedure of Steps 3, 4 and 5 of Example 13) and conc. HCl (10 drops) in MeOH (20 mL) was stirred at room temperature for 2 h. Water was poured into the mixture and left to precipitate overnight in the refrigerator. The precipitate was collected, washed with hexane and dried to give 1-(5-hydroxy-6,7-dimethyl-benzofuran-2-yl)-ethanone as a light brown solid (490 mg). $^1$H NMR (CDCl$_3$, 300 MHz) δ: 7.38 (s, 1H), 6.89 (s, 1H), 4.88 (1H, OH), 2.60, 2.50, 2.31 (3s, 9H) ppm. $^{13}$C NMR (CDCl$_3$, 75 MHz) δ: 192.76, 155.45, 155.13, 153.72, 130.29, 127.27, 124.75, 117.44, 106.18, 29.30, 15.56, 15.28 ppm. MS (m/z): 205 (M+H$^+$).

Example 15

1-(3-Bromo-5-hydroxy-6,7-dimethyl-benzofuran-2-yl)-ethanone

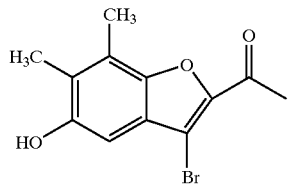

To a solution of 1-[6,7-dimethyl-5-(tetrahydro-pyran-2-yloxy)-benzofuran-2-yl]-ethanone (200 mg) in chloroform (20 mL) was added bromine (120 mg). After 1 h, the solution was washed with water and dried over MgSO$_4$ and concentrated. The residue was purified by silica gel column eluting with 10% hexane in DCM to give 1-(3-Bromo-5-hydroxy-6,7-dimethyl-benzofuran-2-yl)-ethanone, as a yellow solid. $^1$H NMR (CDCl$_3$, 300 MHz) δ: 7.38 (s, 1H), 5.55 (s, 1H, OH), 2.60, 2.50, 2.31 (3s, 9H) ppm. MS (m/z): 283, 285 (M+H$^+$).

Example 16

2-Bromo-1-(5-acetoxy-6,7-dimethyl-benzofuran-2-yl)-ethanone

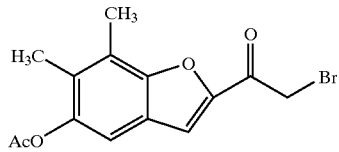

1-(5-Acetoxy-6,7-dimethyl-benzofuran-2-yl)-ethanone (83 mg) (prepared from 1-(5-hydroxy-6,7-dimethyl-benzofuran-2-yl)-ethanone from Example 14 with acetanhydride and pyridine), was dissolved in chloroform (10 mL). Bromine (50 mg) was added and the solution was stirred at 70° C. for 10 min. When the color of bromine disapeared, the mixture was evaporated to dryness. The residue was purified by silica gel column eluting with 30% EtOAc in hexane to give 85 mg of 2-bromo-1-(5-acetoxy-6,7-dimethyl-benzofuran-2-yl)-ethanone as a white solid. $^1$H NMR (CDCl$_3$, 300 MHz) δ: 7.58 (s, 1H), 7.26 (s, 1H), 4.43 (s, 2H), 2.51, 2.37, 2.21 (3s, 9H) ppm. $^{13}$C NMR (CDCl$_3$, 75 MHz) δ: 182.55, 170.13, 153.71, 150.74, 146.81, 131.21, 124.51, 122.92, 115.15, 113.28, 30.69, 21.27, 13.54, 12.80 ppm.

Example 17

Acetic Acid 6,7-Dimethyl-2-(2-morpholin-4-yl-acetyl)-benzofuran-5-yl Ester

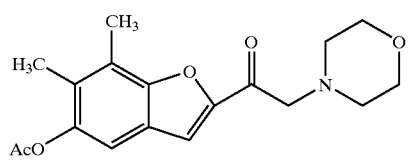

A solution of 2-bromo-1-(5-acetoxy-6,7-dimethyl-benzofuran-2-yl)-ethanone (47 mg) from Example 16, morpholine (15 mg), and potassium carbonate (25 mg) in acetone (10 mL) was stirred at room temperature for 30 min. It was then evaporated to dryness, and the residue was purified by silica gel column eluting with 5% MeOH in DCM to give 43 mg of acetic acid 6,7-dimethyl-2-(2-morpholin-4-ylacetyl)-benzofuran-5-yl ester as an oil. Conversion into the HCl salt gave a yellow solid. $^1$H NMR (CDCl$_3$, 300 MHz) δ: 7.60 (s, 1H), 7.20 (s, 1H), 3.78 (s+t, 6H), 2.64 (m, 4H), 2.50 (s, 3H), 2.40 (s, 3H), 2.20 (s, 3H) ppm. $^{13}$C NMR (CD$_3$OD, 75 MHz) (as HCl salt) δ: 180.94, 170.31, 153.65, 150.33, 147.19, 131.94, 124.33, 122.34, 116.04, 113.59, 63.74, 60.89, 53.28, 19.64, 12.18, 12.22 ppm. M/S 332 (M+H$^+$).

Example 18

1-(5-Hydroxy-6,7-dimethyl-benzofuran-2-yl)-2-morpholin-4-yl-ethanone

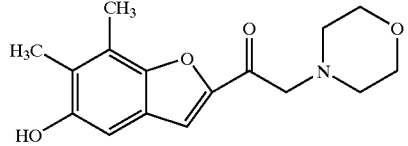

A solution of acetic acid 6,7-dimethyl-2-(2-morpholin4-yl-acetyl)-benzofuran-5-yl ester (23 mg), prepared as in Example 17, in MeOH (10 mL) was stirred while sodium bicarbonate (10 mg) was added. Then the mixture was stirred at RT overnight, followed by evaporation to dryness. The residue was purified by silica gel column, eluting with 5% MeOH in dichloromethane to give 11 mg of 1-(5-hydroxy-6,7-dimethyl-benzofuran-2-yl)-2-morpholin-4-yl-ethanone as an oil. Conversion into HCl salt gave a yellow solid. $^1$H NMR (CD$_3$OD, 300 MHz) δ: 7.60 (s, 1H), 7.20 (s, 1H), 3.78 (m, 6H), 2.64 (m, 4H), 2.50 (s, 3H), 2.40 (s, 3H) ppm. $^{13}$C NMR (CDCl$_3$, 75 MHz) δ: 187.98, 170.20, 153.31, 152.29, 146.58, 130.44, 124.53, 122.80, 114.36, 113.15, 64.69, 53.79, 21.28, 13.47, 12.86 ppm. M/S 290 (M+H$^+$).

Example 19

2-(1-Hydroxy-2-morpholin-4-yl-ethyl)-6,7-dimethyl-benzofuran-5-ol

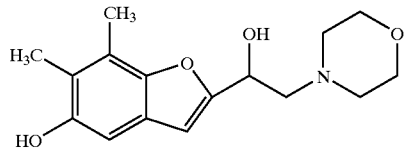

A solution of acetic acid 6,7-dimethyl-2-(2-morpholin4-yl-acetyl)-benzofuran-5-yl ester (35 mg), prepared as in Example 17, in MeOH (10 mL) was stirred while NaBH4 (40 mg) was added, and the mixture was stirred at room temperature for an additional 4 h. The mixture was poured into water, and extracted with ethylacetate. The organic layer was dried over MgSO$_4$ and evaporated. The residue was purified by silica gel column eluting with 5% MeOH in DCM to give 21 mg of 2-(1-hydroxy-2-morpholin-4-yl-ethyl)-6,7-dimethyl-benzofuran-5-ol as an oil. Conversion into HCl salt gave a yellow solid. $^1$H NMR (CD$_3$OD, 300 MHz) δ: 6.77 (s, 1H), 6.67 (s, 1H), 5.29 (dd, J=10.4, 3.3 Hz, 1H), 4.04 (m, 2H), 3.85 (q, 2H), 3.70–3.50 (m, 4H), 3.30 (m, 2H), 2.40 (s, 3H), 2.20 (s, 3H) ppm. $^{13}$C NMR (CD$_3$OD, 75 MHz) (as HCl salt) δ: 154.72, 151.88, 149.40, 125.02, 121.67, 120.21, 104.51, 102.50, 63.77, 63.69, 61.70, 60.19, 53.82, 51.28, 11.24, 11.10 ppm. M/S 292 (M+H$^+$).

Example 20

2-(5-Hydroxy-6,7-dimethyl-benzofuran-2-yl)-4-methyl-morpholin-2-ol

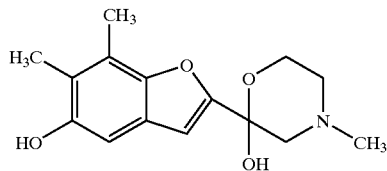

A mixture of 2-bromo-1-(5-acetoxy-6,7-dimethyl-benzofuran-2-yl)-ethanone (30 mg), methylaminoethanol (7 mg), and potassium carbonate (20 mg) in acetone (10 mL) was stirred at RT for 1 h. The mixture was poured into water and extracted with ethylacetate. The organic layer was dried and evaporated followed by purification by silica gel column chromatography eluting with 5% MeOH in DCM to give 20 mg of 2-(5-hydroxy-6,7-dimethyl-benzofuran-2-yl)-4-methyl-morpholin-2-ol as an oil, and was converted into the HCl salt. The NMR showed an equilibrium of the hemiketal and ketone form. $^1$H NMR (CDCl$_3$, 300 MHz) δ: 7.51, 7.26 (2s, combined, 1H), 7.06, 6.87 (2s, combined 1H), 7.06, 6.87 (2s, combined 1H) 4.2–3.7 (m, 2H), 3.2–2.8 (m, 4H), 2.5–2.0 (m, 12H) ppm. $^{13}$C NMR (CDCl$_3$, 75 MHz) δ: 189.26, 170.43, 170.18, 156.79, 152.53, 145.71, 125.79, 125.39, 124.46, 121.73, 113.88, 113.14, 111.52, 104.28, 92.48, 63.55, 62.62, 61.11, 59.68, 54.75, 46.37, 21.30, 13.48, 13.02, 12.90 ppm. M/S 320 (M+H$^+$).

Example 21

5-Hydroxy-6,7-dimethyl-benzofuran-2-carboxylic Acid Methyl Ester

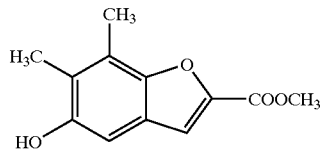

Step 1:

2,5-Dihydroxy-3,4-dimethyl-benzaldehyde (2.0 g) was dissolved in dichloromethane (50 mL) and 3,4-dihydro-2H-pyran (1.5 g) was added followed by addition of p-toluenesulfonic acid monohydrate (200 mg). The solution was stirred at room temperature for 1 hour and quenched by adding sodium bicarbonate solution (1 mL). Then the dichloromethane solution was dried over MgSO$_4$ and concentrated. The residue was purified by silica gel column eluting with hexane and ethyl acetate (8:2) to give 1.5 g of 2-hydroxy-3,4-dimethyl-5-(tetrahydro-pyran-2-yloxy)-benzaldehyde product.

Step 2

A mixture of 2-hydroxy-3,4-dimethyl-5-(tetrahydro-pyran-2-yloxy)-benzaldehyde (150 mg) from Step 1, methyl bromoacetate (180 mg) and potassium-carbonate (200 mg) in DMF (10 mL) was stirred at room temperature for 2 hours. Then the solution was poured into water and extracted with ethylacetate. The ethyl acetate was washed with water and brine, dried over MgSO$_4$ and concentrated. The residue was purified by silica gel column eluting with hexane and ethyl acetate (9:1) to give 100 mg of [6-formyl-2,3- dimethyl-4-(tetrahydro-pyran-2-yloxy)-phenoxy]-acetic acid methyl ester, which was then dissolved in DMF (15 mL). To this solution was added cesium carbonate (200 mg) and the mixture was stirred at room temperature overnight. Then the solution was poured into water and extracted with ethylacetate. The organic layer was washed with water and brine, dried over $MgSO_4$ and concentrated to give 6,7-dimethyl-5-(tetrahydro-pyran-2-yloxy)-benzofuran-2-carboxylic acid methyl ester. The tetrahydropyranyl ether was dissolved in methanol, p-toluenesulfonic acid monohydrate (20 mg) was added, and the solution was stirred at room temperature for an additional 30 min. After the addition of a small amount of $NaHCO_3$, the methanol was evaporated. The residue was purified by silica gel column chromatography, eluting with hexane and ethyl acetate (7:3) to give 30 mg of 5-hydroxy-6,7-dimethyl-benzofuran-2-carboxylic acid methyl ester. $^1$H NMR ($CDCl_3$, 300 MHz) δ: 7.39 (s, 1H), 6.87 (s, 1H), 4.75 (s, 1H), 3.95 (s, 3H), 2.50, 2.26 (2s, 6H) ppm.

Example 22

5-Hydroxy-6,7-dimethyl-benzofuran-2-carboxylic Acid 2-[2-(2-methoxyethoxy-ethoxy)-ethoxy]-ethyl Ester

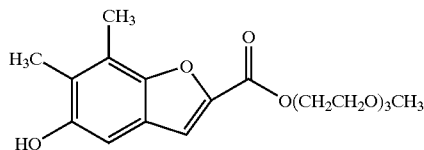

A mixture of acid (50 mg), 2-[2-(2-methoxy-ethoxy)-ethoxy]-ethanol (100 µL), DCC (120 mg), DMAP (50 mg) in DCM (20 mL) was stirred at RT for overnight. The mixture was poured into water and extracted with ethylacetate. The organic layer was washed with water and brine, dried over $MgSO_4$ and concentrated. The residue was purified by silica gel column chromatopraphy eluting with 40% EtOAc in hexane to give the tetrahydropyranyl ether of 5-hydroxy-6,7-dimethyl-benzofuran-2-carboxylic acid 2-[2-(2-methoxy-ethoxy)-ethoxy]-ethyl ester (40 mg). This intermediate was dissolved in MeOH, diluted HCl was added, and the mixture was stirred for 30 min. The mixture was poured into water and extracted with ethylacetate. The organic layer was washed with water and brine, dried over MgSO4 and concentrated. Purification by silica gel column eluting with 2% MeOH in DCM gave 30 mg of 5-hydroxy-6,7-dimethyl-benzofuran-2-carboxylic acid 2-[2-(2-methoxy-ethoxy)-ethoxy]-ethyl ester. $^1$HNMR ($CDCl_3$, 300 MHz) δ: 7.27 (s, 1H), 6.84 (s, 1H), 6.30 (br., 1H) 4.50 (m, 2H), 3.87 (m, 2H), 3.71–3.50 (m, 8H), 3.35 (s, 3H), 2.42 (s, 3H), 2.26 (s, 3H) ppm. $^{13}$CNMR ($CDCl_3$, 75 MHz) δ: 159.33, 150.91, 150.11, 143.97, 124.82, 123.33, 121.14, 102.70, 71.04, 70.23, 70.15, 70.11, 68.76, 63.74, 58.56, 11.86, 11.81 ppm. MS: 375.1 (M+H$^+$).

Similarly by following the procedure described above but replacing 2-[2-(2-methoxy-ethoxy)-ethoxy]-ethanol with the appropriate alcohol the following compounds were prepared:

Geraniol gave 5-hydroxy-6,7-dimethyl-benzofuran-2-carboxylic acid 3,7-dimethyl-octa-2,6-dienyl ester; $^1$HNMR ($CDCl_3$, 300MHz) δ: 7.54 (s, 1H), 7.07 (s, 1H), 5.48 (m, 1H), 5.36 (s,1H), 5.09 (m, 1H), 4.87 (m, 2H), 2.49 (s, 3H), 2.28 (s, 3H), 2.08 (m, 4H), 1.80, 1.60, 1.39 (3s, 9H) ppm. $^{13}$CNMR ($CDCl_3$, 75 MHz) δ: 159.67, 150.50, 150.28, 144.67, 142.55, 131.49, 124.38, 123.53, 123.27, 121.39, 117.48, 113.59, 102.87, 61.79, 39.14, 25.83, 25.26, 17.28, 16.19, 11.89, 11.94 ppm. MS: 343 (M+H$^+$).

2-Aminoethanol gave 5-hydroxy-6,7-dimethyl-benzofuran-2-carboxylic acid (2-hydroxy-ethyl)-amide; 1HNMR(DMSO-d6, 300MHz) δ: 9.3 (br., 1H), 8.42 (s, 1H), 7.25 (s, 1H), 6.83 (s, 1H), 4.77 (br., 1H) 3.47 (m, 4H), 2.37 (s, 3H), 2.11 (s, 3H) ppm. $^{13}$CNR (DMSO-d6, 75 MHz) δ: 158.90, 151.77, 148.24, 147.89, 123.98, 123.77, 120.63, 109.69, 102.62, 59.44, 12.20, 11.95 ppm. MS 250 (M+H+).

2-(2-Hydroxy-ethylamino)-ethanol gave 5-hydroxy-6,7-dimethyl-benzofuran-2-carboxylic acid bis-(2-hydroxy-ethyl)-amide. $^1$HNMR ($CD_3OD$, 300 MHz) δ: 7.26 (s, 1 H), 6.83 (1 H), 3.90–3.70 (m, 8H), 2.40 (s, 3H), 2.23 (s, 3H)ppm. $^{13}$CNMR($CD_3OD$, 75MHz) δ: 161.71, 151.76, 148.60, 147.35, 123.77, 123.25, 119.93, 112.09, 101.73, 60.29, 58.78, 51.76, 50.27, 10.49, 10.43ppm. MS 294 (M+H$^+$).

Morpholine gave (5-Hydroxy-6,7-dimethyl-benzofuran-2-yl)-morpholin-4-yl-methanone; $^1$HNMR (DMSO-d$_6$-D$_2$O, 300 MHz) δ: 7.22 (s, 1H), 5.88 (1H), 3.65 (m, 8H), 2.34 (s, 3H), 2.34 (s, 3H), 2.15 (s, 3H) ppm. MS 276 (M+H$^+$).

Example 23

2-Hydroxymethyl-6,7-dimethyl-benzofuran-5-ol

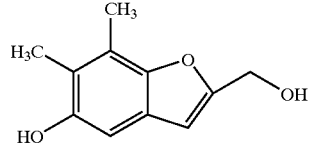

5-Hydroxy-6,7-dimethyl-benzofuran-2-carboxylic acid methyl ester (231 mg) prepared as in Example 2, was dissolved in THF and lithium alumininum hydride (93 mg) was added. The mixture was stirred at room temperature for 4 h. Then the solution was poured into water and extracted with ethylacetate. The ethyl acetate was washed with water and brine, dried over $MgSO_4$ and concentrated. Purification by silica gel column eluting with 50% EtOAc in hexane gave 89 mg of 2-Hydroxymethyl-6,7-dimethyl-benzofuran-5-ol. $^1$HNMR ($CD_3OD$, 300MHz) δ: 6.75, 1H), 6.47 (s, 1H), 4.61 (s, 2H), 2.37 (s, 3H), 2.20 (s, 3H) ppm. $^{13}$CNMR ($CD_3OD$, 75 MHz) δ: 155.87, 150.51, 148.68, 124.69, 119.93, 119.20, 103.01, 101.62, 56.32, 10.43, 10.29 ppm. MS: 175 (M—OH)$^+$.

Example 24

6,7-Dimethyl-2-(4-nitro-phenyl)-benzofuran-5-ol

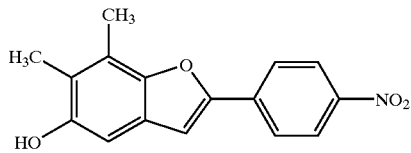

A mixture of 2-hydroxy-3,4-dimethyl-5-(tetrahydro-pyran-2-yloxy)-benzaldehyde (200 mg) prepared as in Example 21, p-nitrobenzyl bromide (200 mg) and potassium carbonate (220 mg) in DMF (10 mL) was stirred overnight at room temperature. Then the solution was poured into water and extracted with ethylacetate. The ethylacetate was washed with water and brine and dried over $MgSO_4$ and concentrated. The residue was purified by silica gel column eluting with hexane: ethylacetate (8:2) to give 242 mg of the tetrahydropyranyl ether of 6,7-Dimethyl-2-(4-nitro-phenyl)-benzofuran-5-ol. A mixture of the ether (240 mg) and NaOMe (17 mg) in DMF (10 mL) was stirred at 70° C. for 2 h. Then the solution was poured into water and extracted with ethylacetate. The organic layer was washed with water and brine, dried over MgSO4 and concentrated. The residue was dissolved in MeOH and p-toluenesulfonic acid monohydrate (20 mg) was added and the solution was stirred at room temperature for 1.5 h. Ater the addition of a small amount of $NaHCO_3$, the methanol was evaporated, and the residue was purified by silica gel column chromatography eluting with hexane and ethyl acetate (7:3) to give 170 mg of 6,7-dimethyl-2-(4-nitro-phenyl)-benzofuran-5-ol. $^1H$ NMR ($CDCl_3$-DMSO-$d_6$, 300 MHz) δ: 9.16 (s, 1H), 8.28 (d, J=8.1 Hz, 2H), 8.06 (d, J=8.1 Hz, 2H), 7.46 (s, 1H), 6.87 (s, 1H), 2.44, 2.18 (2s, 6H) ppm. $^{13}C$ NMR (CDCl3-DMSO-d6, 75 MHz) δ: 152.87, 152.57, 149.68, 147.15, 137.19, 126.16, 125.64, 125.07, 123.56, 120.66, 107.03, 103.13, 12.92, 12.84 ppm.

Similarly following the procedure described above, the following compound was prepared: 4-(5-Hydroxy-6,7-dimethyl-benzofuran-2-yl)-benzonitrile; $^1H$ NMR (DMSO-$d_6$, 300 MHz) δ: 9.24 (s, 1H), 8.00 (d, J=8.0 Hz, 2H), 7.90 (d, J=8.0 Hz, 2H), 7.47 (s, 1H), 6.87 (s, 1H), 2.41, 2.18 (2s, 6H), ppm. $^{13}C$ NMR (DMSO-$d_6$, 75 MHz) δ: 152.92, 152.82, 149.36, 135.22, 133.75, 126.19, 125.50, 123.17, 120.75, 119.72, 110.80, 106.30, 103.10, 12.95, 12.84 ppm.

Example 25

5-Hydroxy-6,7-dimethyl-benzofuran-2-carbaldehyde

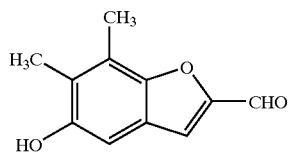

A mixture of 2-hydroxy-3,4-dimethyl-5-(tetrahydropyran-2-yloxy)-benzaldehyde (300 mg), bromoacetaldhyde dimethyl acetal (300 mg) and potassium carbonate (330 mg) in DMF (10 mL) was stirred at 140° C. for 2 h. Then the solution was poured into water and extracted with ethylacetate. The organic layer was washed with water and brine, dried over MgSO4 and concentrated. The residue was purified by silica gel column chromatography eluting with hexane:ethylacetate (8:2) to give 102 mg of the tetrahydropyranyl ether of 5-hydroxy-6,7-dimethyl-benzofuran-2-carbaldehyde. A solution of this intermediate (100 mg) in acetic acid (15 mL) was refluxed for 2 h. Then acetic acid was evaporated and the residue was purified on silica gel column chromatography eluting with 30% ethyl acetate in hexane to give 70 mg of 5-hydroxy-6,7-dimethyl-benzofuran-2-carbaldehyde. Further purification by silica gel eluting with dichloromethane and ethyl acetate (9:1) gave a pure product (36 mg). $^1H$ NMR (DMSO-$d_6$, 300 MHz) δ: 9.75 (s, 1H), 9.55 (s, 1H), 7.79 (s, 1H), 7.00 (s, 1H), 2.39 (s, 3H), 2.20 (s, 3H) ppm. $^{13}C$ NMR (DMSO-d6, 75 MHz) δ: 181.06, 181.02, 153.46, 152.89, 150.56, 128.00, 124.47, 121.72, 120.79, 104.14, 13.34, 12.84 ppm.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

We claim:

1. A compound represented by Formula I

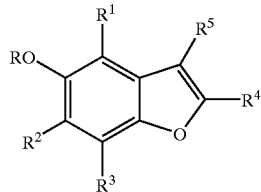

Formula I wherein:

$R^1$ is: hydrogen, optionally substituted ($C_1$–$C_6$)-alkyl, optionally substituted ($C_2$–$C_{10}$)-alkenyl, optionally substituted aryl, (optionally substituted ($C_1$–$C_6$)-alkoxy)carbonyl, or halogen;

$R^2$ and $R^3$ are independently selected from optionally substituted ($C_1$–$C_6$)-alkyl, optionally substituted ($C_2$–$C_{10}$)-alkenyl, or optionally substituted ($C_3$–$C_8$)-cycloalkyl;

$R^4$ is: hydrogen, optionally substituted aryl, (optionally substituted($C_1$–$C_6$)-alkyl)carbonyl, (optionally substituted aryl)carbonyl, (optionally substituted heterocyclyl)carbonyl, (optionally substituted heterocyclylalkyl)carbonyl, (optionally substituted ($C_1$–$C_6$)-alkoxy)carbonyl, (optionally substituted ($C_2$–$C_{10}$)-alkenyloxy)carbonyl, (optionally substituted amino)carbonyl, carboxy, formyl, or hydroxy (optionally substituted)($C_1$–$C_6$)-alkyl;

$R^5$ is: hydrogen, ($C_1$–$C_6$)-alkyl, ($C_2$–$C_{10}$)-alkenyl, (optionally substituted alkoxy)carbonyl, carboxy, (optionally substituted amino)carbonyl, or optionally substituted aryl;

provided that one of $R^4$ or $R^5$ is hydrogen, and that when $R^4$ is hydrogen $R^5$ is not hydrogen, and when $R^5$ is hydrogen $R^4$ is not hydrogen;

R is hydrogen, ($C_1$–$C_6$)-alkyl, ($C_1$–$C_6$)-alkylcarbonyl, phosphoryl, or polyalkoxy; or R and $R^1$ with the atoms to which they are attached form an optionally substituted ring;

single stereoisomers, mixtures of stereoisomers, and the pharmaceutically acceptable salts thereof.

2. The compound of claim 1, wherein $R^1$ is hydrogen or halogen.

3. The compound of claim 1, wherein $R^2$ and $R^3$ are ($C_1$–$C_6$)-alkyl.

4. The compound of claim 3, wherein $R^1$ is hydrogen.

5. The compound of claim 4, wherein R is hydrogen.

6. The compound of claim 5, wherein $R^5$ is optionally substituted phenyl, and wherein the one or more substitutents are independently selected from ($C_1$–$C_6$)-alkyl, ($C_1$–$C_6$)-alkoxy, hydroxy, carboxy, ($C_1$–$C_6$)-alkoxycarbonyl, nitro, halo, and cyano.

7. The compound of claim 6, wherein $R^4$ is hydrogen.

8. The compound of claim 5, wherein $R^4$ is optionally substituted phenyl and wherein the one or more substituents are independently selected from $(C_1-C_6)$-alkyl, $(C_1-C_6)$-alkoxy, hydroxy, carboxy, $(C_1-C_6)$-alkoxycarbonyl, nitro, halo, and cyano.

9. The compound of claim 8 wherein $R^4$ is 4-nitrophenyl or 4-cyanophenyl, and $R^5$ is hydrogen.

10. The compound of claim 5, wherein $R^4$ is formyl, optionally substituted phenylcarbonyl, optionally substituted $(C_1-C_6)$-alkylcarbonyl, or hydroxy(optionally substituted $(C_1-C_6)$-alkyl, wherein the one or more substituents are independently selected from hydroxy, hydroxyalkyl, halogen, cyano, and heterocyclyl.

11. The compound of claim 10, wherein $R^4$ is formyl, phenylcarbonyl, acetyl, bromoacetyl, morpholin-1-yl-acetyl, hydroxymethyl, 1-hydroxy-2-morpholiny4-yl ethyl, or 6-hydroxy-3-methyl-[1,3]oxazinan-6-yl; and $R^5$ is hydrogen.

12. The compound of claim 5, wherein $R^4$ is $(C_1-C_6)$-alkoxycarbonyl, $(C_2-C_{10})$-alkenyloxycarbonyl, or optionally substituted aminocarbonyl, wherein one or more substituents are independently selected from $(C_1-C_6)$-alkyl and hydroxy-$(C_1-C_6)$-alkyl.

13. The compound of claim 12, wherein $R^4$ is bis-(2-hydroxy-ethyl)-amide, 2-hydroxy-ethyl-amide, carboxylic acid; carboxylic acid methyl ester; carboxylic acid 3,7dimethyl-octa-2,6-dienyl ester; [2-(2-methoxy-ethoxy)-ethoxy]ethyl ester or morpholin-1-yl carbonyl; and $R^5$ is hydrogen.

14. The compound of claim 1, wherein R and $R^1$ with the atoms to which they are attached form an optionally substituted ring.

15. The compound of claim 14, wherein R and $R^1$ with the atoms to which they are attached form a furan ring substituted with a phenyl, said phenyl being optionally substituted with one or more substituents independently selected from alkyl, alkenyl, hydroxy, alkoxy, nitro, cyano, carboxy, ester, haloalkyl, and halo.

16. The compound of selected from the group:
(5-Hydroxy-3,6,7-trimethyl-benzofuran-2-yl)-phenyl-methanone;
(5-Hydroxy-6,7-dimethyl-benzofuran-2-yl)-morpholin-4-yl-methanone;
1-(5-Hydroxy-6,7-dimethyl-benzofuran-2-yl)-ethanone;
Acetic acid 2-(2-bromo-acetyl)-6,7-dimethyl-benzofuran-5-yl ester;
2-(i-Hydroxy-2-morpholin-4-yl-ethyl)-6,7-dimethyl-benzofuran-5-ol;
Acetic acid 6,7-dimethyl-2-(2-morpholin-1-yl-acetyl)-benzofuran-5-yl ester;
Acetic acid 2-(6-hydroxy-3-methyl-[1,3]oxazinan-6-yl)-6,7-dimethyl-benzofuran-5-yl ester;
1-(5-Hydroxy-6,7-dimethyl-benzofuran-2-yl)-2-morpholin-4-yl-ethanone;
1-(4-Bromo-5-hydroxy-6,7-dimethyl-benzofuran-2-yl)-ethanone;
2-Hydroxymethyl-6,7-dimethyl-benzofuran-5-ol;
6,7-Dimethyl-3-phenyl-benzofuran-5-ol;
6,7-Dimethyl-2-(4-nitro-phenyl)-benzofuran-5-ol;
5-Hydroxy-6,7-dimethyl-benzofuran-2-carbaldehyde;
4-(5-Hydroxy-6,7-dimethyl-benzofuran-2-yl)-benzonitrile;
5-Hydroxy-6,7-dimethyl-benzofuran-2-carboxylic acid;
5-Hydroxy-6,7-dimethyl-benzofuran-2-carboxylic acid methyl ester;
5-Hydroxy-6,7-dimethyl-benzofuran-2-carboxylic acid 3,7-dimethyl-octa-2,6-dienyl ester;
5-Hydroxy-6,7-dimethyl-benzofuran-2-carboxylic acid bis-(2-hydroxy-ethyl)-amide;
5-Hydroxy-6,7-dimethyl-benzofuran-2-carboxylic acid 2-[2-(2-methoxy-ethoxy)-ethoxy]-ethyl ester;
5-Hydroxy-6,7-dimethyl-benzofuran-2-carboxylic acid (2-hydroxy-ethyl)-amide;
3-(4-Methoxy-phenyl)-6,7-dimethyl-benzofuran-5-ol;
3-(4-Chloro-phenyl)-6,7-dimethyl-benzofuran-5-ol;
3-(4-Fluoro-phenyl)-6,7-dimethyl-benzofuran-5-ol;
4,5-Dimethyl-1,8-diphenyl-benzo[1,2-b;4,3-b']difuran;
1,8-Bis-(4-fluoro-phenyl)-4,5-dimethyl-benzo[1,2-b;4,3-b']difuran; and
1,8-Bis-(4-methoxy-phenyl)-4,5-dimethyl-benzo[1,2-b;4,3-b']difuran.

17. A pharmaceutical or cosmetic formulation comprising a compound of claim 1 admixed with at least one acceptable excipient.

18. A method of treatment for a mammal suffering from a condition characterized by oxidative stress, comprising administering a therapeutically effective amount of a compound of claim 1.

19. The method of claim 18, wherein the condition is selected from stroke, cerebral ischemia, retinal ischemia, myocardial infarction, chronic heart failure, post-surgical cognitive dysfunctions, peripheral neuropathy, spinal cord injury, head injury, and surgical trauma.

20. The method of claim 18, wherein the condition involves inflammatory or autoimmune components.

21. The method of claim 18, wherein the condition is a dermatologic condition.

22. The method of claim 21, wherein the condition is selected from regulating skin condition, regulating the signs of skin aging, regulating hair growth modulation, and treating contact dermatitis, skin pigmentation, irritation including retinoid induced irritation, acne, psoriasis, age-related damage and damage resulting from harmful (UV) radiation, stress or fatigue.

23. A method of treatment for a mammal suffering from a condition characterized by oxidative stress, comprising administering a therapeutically effective amount of a compound of claim 16.

24. The method of claim 23, wherein the condition is selected from stroke, cerebral ischemia, retinal ischemia, myocardial infarction, chronic heart failure, post-surgical cognitive dysfunctions, peripheral neuropathy, spinal cord injury, head injury, and surgical trauma.

25. The method of claim 23, wherein the condition involves inflammatory or autoimmune components.

26. The method of claim 23, wherein the condition is selected from regulating skin condition, regulating the signs of skin aging, regulating hair growth modulation, and treating contact dermatitis, skin pigmentation, irritation including retinoid induced irritation, acne, psoriasis, age-related damage or damage resulting from harmful (UV) radiation, stress or fatigue.

27. A method for ameliorating a symptom of an inflammatory condition in an individual subject to an inflammatory condition comprising administering to the individual a composition comprising a compound of claim 1, in an amout effective to reduce the level of CRP associated with an inflammatory condition.

28. The method of claim 27, wherein said inflammatory condition is selected from the group consisting of cardiovascular inflammatory condition, respiratory inflammatory condition, sepsis, diabetes, muscle fatigue, systemic lupus erythematosis (SLE), end stage renal disease (ERSD) periodontal disease, and inflammatory skin conditions.

* * * * *